US008778351B2

(12) United States Patent
Rose et al.

(10) Patent No.: US 8,778,351 B2
(45) Date of Patent: Jul. 15, 2014

(54) COMBINED HUMAN PAPILLOMAVIRUS VLP/GENE DELIVERY SYSTEM AND USE THEREOF AS A VACCINE FOR PROPHYLAXIS AND IMMUNOTHERAPY OF INFECTIOUS DISEASES AND TUMORS

(75) Inventors: Robert C. Rose, Geneseo, NY (US); Christine Malboeuf, Sharon, MA (US); Young-Eun Ellen Lee, Levittown, NY (US)

(73) Assignee: University of Rochester, Rochester, NY (US)

( * ) Notice: Subject to any disclaimer, the term of this patent is extended or adjusted under 35 U.S.C. 154(b) by 1101 days.

(21) Appl. No.: 12/439,338

(22) PCT Filed: Aug. 30, 2007

(86) PCT No.: PCT/US2007/077297
§ 371 (c)(1),
(2), (4) Date: Oct. 22, 2009

(87) PCT Pub. No.: WO2008/082719
PCT Pub. Date: Jul. 10, 2008

(65) Prior Publication Data
US 2010/0092504 A1    Apr. 15, 2010

Related U.S. Application Data

(60) Provisional application No. 60/824,010, filed on Aug. 30, 2006.

(51) Int. Cl.
*A61K 39/12* (2006.01)
*A61K 39/23* (2006.01)
*C12N 15/62* (2006.01)

(52) U.S. Cl.
USPC ............... 424/192.1; 424/204.1; 424/208.1; 424/188.1; 536/23.4; 536/23.72

(58) Field of Classification Search
None
See application file for complete search history.

(56) References Cited

U.S. PATENT DOCUMENTS

| | | | |
|---|---|---|---|
| 5,618,536 | A | 4/1997 | Lowy et al. |
| 5,855,891 | A | 1/1999 | Lowy et al. |
| 6,599,508 | B1 | 7/2003 | Gissmann et al. |
| 6,599,739 | B1 | 7/2003 | Lowy et al. |
| 7,247,433 | B2 | 7/2007 | Rose |
| 2004/0131638 | A1* | 7/2004 | Debrus et al. ............ 424/202.1 |

FOREIGN PATENT DOCUMENTS

| | | |
|---|---|---|
| WO | 94/20137 A1 | 9/1994 |
| WO | 99/15630 A1 | 4/1999 |
| WO | 99/61052 A2 | 12/1999 |
| WO | 02/04007 A2 | 1/2002 |
| WO | 03/018622 A1 | 3/2003 |

OTHER PUBLICATIONS

Unckell et al, Journal of Virology, 1997, vol. 71, No. 4, pp. 2934-2939.*
Liu et al, Virology, 2000, vol. 273, pp. 374-382.*
Dale et al. Chimeric human papilloma virus-simian/human immunodeficiency virus virus-like-particle vaccines: immunogenicity and protective efficacy in macaques. Virology. Sep. 15, 2002;301(1):176-87.*
Bousarghin et al., Detection of Neutralizing Antibodies Against Human Papillomaviruses (HPV) by Inhibition of Gene Transfer Mediated by HPV Pseudovirions, Journal of Clinical Microbiology 40(3):926-32 (2002).
Combita et al., "Gene Transfer Using Human Papillomavirus Pseudovirions Varies According to Virus Genotype and Requires Cell Surface Heparan Sulfate," FEMS Microbiology Letters 204:183-8 (2001).
Greenstone et al., "Chimeric Papillomavirus Virus-like Particles Elicit Antitumor Immunity Against the E7 Oncoprotein in an HPV16 Tumor Model," 95:1800-5 (1998).
Kämper et al., "A Membrane-Destabilizing Peptide in Capsid Protein L2 Is Required for Egress of Papillomavirus Genomes from Endosomes," Journal of Virology 80(2):759-68 (2006).
Krauzewicz et al., "Sustained ex Vivo and in Vivo Transfer of a Reporter Gene Using Polyoma Virus Pseudocapsids," Gene Therapy 7:1094-102 (2000).
Krauzewicz et al., "Virus-like Gene Transfer into Cells Mediated by Polyoma Virus Pseudocapsids," Gene Therapy 7:2122-31 (2000).
Muller et al., "Chimeric Papillomavirus-like Particles," Virology 234:93-111 (1997).
Peng et al., "Development of a DNA Vaccine Targeting Human Papillomavirus Type 16 Oncoprotein E6," Journal of Virology 78(16):8468-76 (2004).
Rossi et al., "Assembly of Human Papillomavirus Type 16 Pseudovirions in *Saccharomyces cerevisiae*," Human Gene Therapy 11(8):1165-76 (2000).
Touze et al., "In Vitro Gene Transfer Using Human Papillomavirus-like Particles," Nucleic Acids Research 26 (5):1317-23 (1998).
Schafer et al., "Immune Response to Human Papillomavirus 16 L1E7 Chimeric Virus-like Particles: Induction of Cytotoxic T Cells and Specific Tumor Protection," Int. J. Cancer 81:881-8 (1999).
Xu et al., "Papillomavirus Virus-like Particles as Vehicles for the Delivery of Epitopes or Genes," Arch Virol 151:2133-48 (2006).

* cited by examiner

*Primary Examiner* — Mary E Mosher
*Assistant Examiner* — Nick Zou
(74) *Attorney, Agent, or Firm* — LeClairRyan, a Professional Corporation

(57) ABSTRACT

The present invention relates to compositions that contain a chimeric papillomavirus virus-like particle (VLP) in combination with a DNA molecule encoding a protein or polypeptide epitope. The chimeric papillomavirus VLP is assembled from an L1 protein or polypeptide and a chimeric protein or polypeptide containing at least a portion of the L2 protein and a protein or polypeptide including an immunogenic epitope. The composition is useful for inducing an enhanced immune response against a pathogen or a tumor.

19 Claims, 17 Drawing Sheets

A – 50ug of DNA alone (prime and boost)
B – 10ug of cVLPs alone (prime and boost)
C – 10ug of cVLPs + 50ug of DNA (prime and boost)
D – 10ug of 16L1/L2 VLPs + 50ug of DNA (prime and boost)

*cVLPs = 16L1/L2-NefV3F cVLPs*
*DNA = pcDNA3-CRT-NefV3F plasmid*

HIV-1 Con B Nef peptides (15-mer) [ARRRP]
Group 1 – Nef peptide pool I (1-12)
Group 2 – Nef peptide pool II (13-24)
Group 3 – Nef peptide pool III (25-36)
Group 4 – Nef peptide pool IV (37-49)

A – naïve group
B – 50ug of DNA alone
C – 10ug of 16L1/L2N-NefV3F cVLPs alone
D – 10ug of 16L1/L2N-NefV3F cVLPs + 50ug of DNA DNA = pcDNA3-CRT-NefV3-Flag plasmid DNA
All mice received prime (day 0) and boost (day 7)

A – 10ug of cVLPs + 50ug of DNA (prime and boost)
B – 100ug DNA (prime) + 20ug of cVLPs (boost)

cVLPs = 16L1/L2-NefV3F cVLPs
DNA = pcDNA3-CRT-NefV3F plasmid

Group 1 – 10ug of cVLPs + 50ug of DNA (i.p.)
Group 2 – 10ug of cVLPs + 50ug of DNA (i.m.)
cVLPs = 16L1/L2Full-NefV3F cVLPs
DNA = pcDNA3-CRT-NefV3F plasmid

A - 50 ug DNA prime; 50 ug DNA boost
B - 10 ug cVLP prime; 10 ug cVLP boost
C - 50 ug DNA/10 ug cVLP in the same leg; prime and boost
D - 50 ug DNA (left hind leg); 10 ug cVLP (right hind leg) prime and boost

*cVLPs = 16L1/L2N-NefV3F cVLPs*
*DNA = pcDNA3-CRT-NefV3F plasmid*

COMBINED HUMAN PAPILLOMAVIRUS VLP/GENE DELIVERY SYSTEM AND USE THEREOF AS A VACCINE FOR PROPHYLAXIS AND IMMUNOTHERAPY OF INFECTIOUS DISEASES AND TUMORS

The present invention was made with government support under grant T32 AI007169 awarded by the National Institutes of Health. The government has certain rights in the invention.

This application is a national stage application under 35 U.S.C. 371 of PCT/US2007/077297, filed Aug. 30, 2007, and claims the benefit of U.S. Provisional Patent Application Ser. No. 60/824,010, filed Aug. 30, 2006, which is hereby incorporated by reference in its entirety.

FIELD OF THE INVENTION

The present invention relates to methods and compositions for inducing an immune response against a pathogen or tumor.

BACKGROUND OF THE INVENTION

Papillomaviruses cause warts and other hyperproliferative epithelial disorders in humans and other higher vertebrates (Howley et al., "Papillomaviruses and Their Replication," In D. M. Knipe and P. M. Howley (ed.), *Fields Virology*, Lippincott Williams & Wilkins, Philadelphia, 4th ed, vol. 2., pp. 2197-2230 (2001) and Lowy et al., "Papillomaviruses," In D. M. Knipe and P. M. Howley (ed.), *Fields Virology*, Lippincott Williams & Wilkins, Philadelphia p. 4th ed, vol. 2., pp. 2231-2264 (2001)). Thus far, more than 130 genetically distinct human papillomaviruses (HPVs) have been identified and/or partially characterized, each with a characteristic tissue tropism and variable disease potential (de Villiers et al., "Classification of Papillomaviruses," *Virology* 324:17-27 (2004)). Importantly, several mucosal epitheliotropic HPVs have demonstrated oncogenic potential through close association with anogenital malignancies, including uterine cervical carcinoma (Munoz et al., "Against Which Human Papillomavirus Types Shall We Vaccinate and Screen? The International Perspective," *Int J Cancer* 111:278-85 (2004); zur Hausen, H., "Papillomaviruses and Cancer: From Basic Studies to Clinical Application," *Nat Rev Cancer* 2:342-50 (2002)). An estimated 500,000 cases and 275,000 deaths from this disease occur annually among women worldwide (Parkin et al., "Global Cancer Statistics, 2002," *CA Cancer J Clin* 55:74-108 (2005)).

Long-term efforts by several groups to develop safe and effective vaccines for HPV prophylaxis are now bearing fruit (McNeil, C., "Coming Soon: Cervical Cancer Vaccines, and an Array of Public Health Issues," *J Natl Cancer Inst* 98:432-4 (2006)). A tetravalent VLP vaccine formulation (Gardasil™, Merck, Inc.) was approved recently by the U.S. Food and Drug Administration (FDA), and recommended by the Center for Disease Control's (CDC) Advisory Committee on Immunization Practices (ACIP) for universal vaccination of young females (Skjeldestad, F. E., "Prophylactic Quadrivalent Human Papillomavirus (HPV)(Types 6, 11, 16, 18) L1 Virus-Like Particle (VLP) Vaccine (Gardasil™) Reduces Cervical Intraepithelial Neoplasia (CIN) 2/3 Risk," IDSA Annual Conference, October 7th, San Francisco, USA (2005)). A bivalent VLP formulation (Cervarix™, GlaxoSmithKline), which targets HPV types 16 and 18, is expected to be available soon. Wide-spread use of these vaccines can be expected to lead eventually to a marked reduction in incidence and prevalence of genital HPV disease; however, such an effect will likely require several years to occur, as public and private sector groups work to overcome challenges associated with vaccine distribution, particularly in low-resource settings ("WHO Consultation on Human Papillomavirus Vaccines," *Wkly Epidemiol Rec* 80:299-302 (2005)).

Clinical management of genital HPV disease now relies on multiple therapeutic modalities, but all available methods suffer more or less from variable responses to treatment, and variable recurrence rates (ACOG Practice Bulletin, "Clinical Management Guidelines for Obstetrician-Gynecologists No. 61: Human Papillomavirus," *Obstet Gynecol* 105:905-18 (2005)). Thus, there is a need for better therapy. The emergence of VLP technology (Hagensee et al., "Self-assembly of Human Papillomavirus Type 1 Capsids by Expression of the L1 Protein Alone or by Coexpression of the L1 and L2 Capsid Proteins," *Journal of Virology* 67:315-322 (1993); Kirnbauer et al., "Papillomavirus L1 Major Capsid Protein Self-assembles into Virus-like Particles that are Highly Immunogenic," *Proc Natl Acad Sci USA* 89:12180-12184 (1992); and Rose et al., "Expression of Human Papillomavirus Type 11 L1 Protein in Insect Cells: In Vivo and In Vitro Assembly of Viruslike Particles," *Journal of Virology* 67:1936-1944 (1993)), which underlies the prophylactic vaccines (Rose, R. C. (ed.), "Human Papillomavirus Immunology and Vaccine Development," vol. 8. Elsevier, Amsterdam (2002)), has led to the development of several strategies for immunotherapy of established cervical HPV disease (Greenstone et al., "Chimeric Papillomavirus Virus-like Particles Elicit Antitumor Immunity Against the E7 Oncoprotein in an HPV16 Tumor Model," *Proc Natl Acad Sci USA* 95:1800-5 (1998); Muller et al., "Chimeric Papillomavirus-like Particles," *Virology* 234:93-111 (1997)). Because continued expression of the viral E6 and E7 oncoproteins is required for maintenance of the transformed phenotype, such strategies generally have focused on incorporating viral early (E) proteins into VLPs to promote the induction or enhancement of E protein-specific cellular immune responses. For example, an L1-E7 fusion protein has been shown to self-assemble into chimeric VLPs (cVLPs) that can be used to enhance E7-specific cellular immune responses in mice (Schafer et al., "Immune Response to Human Papillomavirus 16 L1-E7 Chimeric Virus-like Particles: Induction of Cytotoxic T Cells and Specific Tumor Protection," *Int J Cancer* 81:881-8 (1999)). In a variation of this theme, L2-E7 or L2-E7-E2 fusion proteins have been generated and incorporated into chimeric VLPs (Greenstone et al., "Chimeric Papillomavirus Virus-like Particles Elicit Antitumor Immunity Against the E7 Oncoprotein in an HPV16 Tumor Model," *Proc Natl Acad Sci USA* 95:1800-5 (1998)) that have been shown to provide similar enhancement of E7- and/or E2-specific responses (Schiller et al., "Papillomavirus-like Particle Vaccines," *J Natl Cancer Inst Monogr* 28:50-4 (2001)).

In addition to using VLPs for delivery of viral early proteins, VLPs consisting of L1 alone have been shown to be capable of delivering plasmid DNA into cells grown in vitro (Combita et al., "Gene Transfer Using Human Papillomavirus Pseudovirions Varies According to Virus Genotype and Requires Cell Surface Heparan Sulfate," *FEMS Microbiol Lett* 204:183-8 (2001) and Touze et al., "In Vitro Gene Transfer Using Human Papillomavirus-like Particles," *Nucleic Acids Research* 26:1317-1323 (1998)), in a manner that appears to be somewhat dependent on genotype (Combita et al., "Gene Transfer Using Human Papillomavirus Pseudovirions Varies According to Virus Genotype and Requires Cell Surface Heparan Sulfate," *FEMS Microbiol Lett* 204:183-8 (2001)). Interestingly, more recent evidence has suggested that VLPs consisting of both the L1 major and L2 minor capsid proteins may be more efficient for DNA delivery than VLPs consisting of L1 alone (Kamper et al., "A Membrane-Destabilizing Peptide in Capsid Protein L2 is Required for Egress of Papillomavirus Genomes from Endosomes," *J Virol* 80:759-68 (2006)). It was shown, for example, that DNA co-delivered with L1 VLPs is retained within endosomes, and that efficient egress from this compartment is dependent on a 23 amino acid sequence located within the L2 carboxyl terminal region. Thus, a potentially important role for L2 in facilitating DNA delivery and expression has been demonstrated in vitro.

It would be desirable to develop a more efficient vaccine that can be used to treat or prevent infectious diseases and various tumors via enhancement of the immune response.

The present invention is directed to overcoming these and other deficiencies in the art.

SUMMARY OF THE INVENTION

A first aspect of the present invention relates to a composition that includes: a papillomavirus virus-like particle including an L1 protein or polypeptide and a chimeric protein or polypeptide that contains at least a portion of an L2 protein and a protein or polypeptide fragment including a first epitope; and a DNA molecule encoding a protein or polypeptide including a second epitope.

A second aspect of the present invention relates to a delivery vehicle that includes a composition according to the first aspect of the present invention.

A third aspect of the present invention relates to the combination of (i) a first composition that includes a papillomavirus virus-like particle having an L1 protein or polypeptide and a chimeric protein or polypeptide that includes at least a portion of an L2 protein and a protein or polypeptide fragment having a first epitope; and (ii) a second composition that includes a DNA molecule encoding a protein or polypeptide fragment having a second epitope.

A fourth aspect of the present invention relates to a method of inducing an immune response against a pathogen or tumor that includes the step of administering a composition according to the first aspect of the present invention to a patient in a manner effective to induce an immune response against the pathogen or tumor that includes the first or second epitope. Preferably, the generated immune response, as a combination of cell-mediated and antibody-mediated immune responses, is greater than the combined individual immune responses generated by either the papillomavirus VLP alone and the DNA molecule alone.

A fifth aspect of the present invention relates to a method of inducing an immune response against a pathogen that includes the steps of: first administering to a patient an effective amount of a papillomavirus virus-like particle including an L1 protein or polypeptide and a chimeric protein or polypeptide that includes at least a portion of an L2 protein and a protein or polypeptide fragment including a first pathogen-specific epitope; and second administering to the patient a DNA molecule encoding a protein or polypeptide that includes a second pathogen-specific epitope; wherein said first and second administering are effective to induce a heightened immune response against the pathogen that is the source of the first and/or second pathogen-specific epitope.

A sixth aspect of the present invention relates to a method of inducing an immune response against a tumor that includes the steps of: first administering to a patient an effective amount of a papillomavirus virus-like particle including an L1 protein or polypeptide and a chimeric protein or polypeptide that includes at least a portion of an L2 protein and a protein or polypeptide fragment including a first tumor-specific epitope; and second administering to the patient a DNA molecule encoding a protein or polypeptide including a second tumor-specific epitope; wherein said first and second administering are effective to induce a heightened immune response against the tumor that is the source of the first and/or second tumor-specific epitope.

As demonstrated herein with in vitro and in vivo results, HPV L1/L2 VLPs, preferably chimeric HPV L1/L2 VLPs, are useful for facilitating delivery and expression of plasmid DNA to antigen presenting cells, and for enhanced induction of immune responses against co-administered plasmid DNA-based immunogens. These results also demonstrate enhanced immune response to infectious diseases other than HPV, including HIV-1, and these results can be extended to other pathogen and tumors that express tumor specific markers. As demonstrated in the accompanying examples the enhanced immune response is not merely additive, but synergistic. In view of the synergistic immune response, the present invention represents a significant improvement in vaccine technology.

DETAILED DESCRIPTION OF THE INVENTION

Figure 1A:
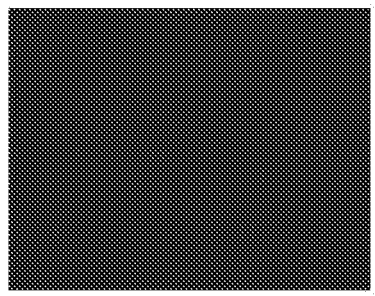
FIGS. 1A-E illustrate the enhancement of VLP-mediated gene delivery in vitro by full-length L2 protein. A GFP reporter plasmid (pEGFP-N1) was applied to HEK293T cells in vitro either alone (FIG. 1A), with Lipofectamine 2000 (FIG. 1B), or in combination with L1 VLPs (FIG. 1C), L1/L2 VLPs (FIG. 1D), or L1/L2N VLPs (FIG. 1E). GFP expression was assessed by fluorescence microscopy 48 hours after plasmid delivery. Images are representative of results obtained in three separate experiments using freshly prepared L1, L1/L2, or L1/L2N VLPs.

The present invention relates generally to novel approaches for immunizing patients against pathogen or tumors, which afford synergistically enhanced immune responses against pathogen infection or tumors. Novel vaccine formulations or combined vaccine deliveries are described herein. Using one or more vaccine formulations, the methods disclosed herein involve the administration of a papillomavirus virus-like particle ("VLP") in combination with a DNA molecule that encodes a protein or polypeptide containing an antigenic epitope specific for a pathogen or tumor. The DNA molecule may or may not be encapsulated within the VLP, but preferably is not. The VLP can be an L1/L2 VLP or, more preferably, a chimeric L1/L2 VLP that expresses an antigenic epitope specific for the pathogen or tumor. Chimeric L1/L2 capsomeres can also be used.

Thus, one aspect of the present invention relates to a composition containing a papillomavirus VLP that is formed of an L1 protein or polypeptide and a chimeric protein or polypeptide containing at least a portion of an L2 protein and a protein or polypeptide having a first epitope. The composition further includes a DNA molecule encoding a protein or polypeptide having a second epitope.

Viruses in the family Papillomaviridae are small, double-stranded, circular DNA tumor viruses. The papillomavirus virion shells consist of the L1 major capsid protein and the L2 minor capsid protein. Expression of L1 protein alone or in combination with L2 protein in eukaryotic or prokaryotic expression systems results in the assembly of VLPs. VLPs are non-infectious and non-replicating, yet morphologically similar to natural virion. Methods for assembly and formation of human papillomavirus VLPs of the present invention are well known in the art (U.S. Pat. No. 6,153,201 to Rose et al.; U.S. Pat. No. 6,165,471 to Rose et al., WO/94/020137 to Rose et al., which are hereby incorporated by reference in their entirety).

As used herein, the papillomavirus VLP can be formed using the L1 and L2 proteins from any animal papillomavirus, or derivatives or fragments thereof. Thus, the known (or hereafter identified) L1 and L2 sequences of human, bovine, canine, feline, rodent, rabbit, etc. papillomaviruses can be employed to prepare the VLPs of the present invention.

In a preferred embodiment of the present invention, the L1 and L2 proteins or polypeptides of the papillomavirus VLP are derived from human papillomaviruses. Preferably, they are derived from HPV-6, HPV-11, HPV-16, HPV-18, HPV-31, HPV-33, HPV-35, HPV-39, HPV-45, HPV-52, HPV-54, HPV-58, HPV-59, HPV-64, or HPV-68.

The L1 protein or polypeptide can be full-length or a polypeptide fragment or derivative thereof that is competent for VLP assembly. The L1 sequences are known for substantially all papillomaviruses identified to date, e.g., HPV-18 (Genbank accessions NC_001357 and X05015, which are hereby incorporated by reference in its entirety); HPV-64 (NC_001676 and U37488, which are hereby incorporated by reference in its entirety); and all other HPV genotypes (e.g., types 6, 11, 16, 31, 33, 35, 39, 45, 52, 54, 58, 59, and 68).

Preferably, the L1 protein or polypeptide is the full length L1 protein. Alternatively, an N-terminal portion of the L1 protein that retains VLP assembly capability can also be used.

In another embodiment, the L1 protein is a chimeric protein or polypeptide including at least a portion of the L1 protein in combination with a protein or polypeptide fragment having an immunogenic epitope. Examples of chimeric L1 proteins expressing an immunogenic epitope that are suitable for use in the present invention include those described by US Patent Application No. US20050118191 to Robinson; WO99/050424 to Stanley et al.; Schafer et al., "Immune Response to Human Papillomavirus 16 L1-E7 Chimeric Virus-like Particles: Induction of Cytotoxic T Cells and Specific Tumor Protection," *Int J Cancer* 81:881-8 (1999); Freyschmidt et al., "Activation of Dendritic Cells and Induction of T-Cell Responses by HPV 16L1/E7 Chimeric Virus-Like Particles are Enhanced by CpG ODN or Sorbital," *Antivir Ther* 9:479-89 (2004); Muller et al., "Chimeric Papillomavirus-like Particles," *Virology* 234:93-111 (1997); Peng et al., "Papillomavirus Virus-Like Particles can Deliver Defined CTL Epitopes to the MHC Class I Pathway," *Virology* 240:147-57 (1998); Liu et al., "Papillomavirus Virus-Like Particles for the Delivery of Multiple Cytotoxic T-Cell Epitopes," *Virology* 273:374-382 (2000); Nieland et al., Chimeric Papillomavirus Virus-Like Particles Induce a Murine Self-Antigen Specific Protective and Therapeutic Anti-Tumor Immune Response," *J. Cell Biochem* 73:145-52 (1999); Slupetzky et al, "Chimeric Papillomavirus-Like Particles Expressing a Foreign Epitope on Capsid Surface Loops," *J Gen Virol* 82:2799-2804 (2001); Zhang et al., "Induction of Mucosal and Systemic Neutralizing Antibodies Against Human Immunodeficiency Virus Type-1 (HIV-1) by Oral Immunization with Bovine Papillomavirus-HIV-1 gp41 Chimeric Virus-Like Particles," *J. Virol* 78:8342-48 (2004), which are hereby incorporated by reference in there entirety). The chimeric L1 protein can contain multiple immunogenic epitopes as described by Liu et al., "Papillomavirus Virus-Like Particles for the Delivery of Multiple Cytotoxic T-Cell Epitopes," *Virology* 273:374-382 (2000), which is hereby incorporated by reference in its entirety. Other chimeric L1 proteins or polypeptides can also be used.

The L2 portion of the chimeric protein can be either full length or a fragment thereof. The L2 sequences are known for substantially all papillomaviruses identified to date, e.g., HPV-18 (Genbank accessions NC_001357 and X05015, which are hereby incorporated by reference in its entirety); HPV-64 (NC_001676 and U37488, which are hereby incorporated by reference in its entirety); and all other HPV genotypes (e.g., types 6, 11, 16, 31, 33, 35, 39, 45, 52, 54, 58, 59, and 68).

The L2 portion of the chimeric protein is preferably either the full-length L2 protein or an N-terminal portion of the L2 protein. In the latter embodiment, the N-terminal portion is preferably at least about half of the full-length L2 protein.

The remaining portion of the chimeric protein is a protein or polypeptide fragment including an immunogenic epitope that is specific for a particular pathogen or tumor. The chimeric L2 protein can contain multiple immunogenic epitopes. This portion of the chimeric protein is described in greater detail below.

Exemplary chimeric proteins of the present invention are described in Example 5 below; US Patent Application No. 20060153864 to Gissman; Silva et al., "Heterologous Boosting Increases Immunogenicity of Chimeric Papillomavirus Virus-Like Particles Vaccines," *Vaccines* 21:3219-3227 (2003); Fausch et al., "Heterologous Papillomavirus Virus-Like Particles and Human Papillomavirus Virus-Like Particle Immune Complexes Activate Human Langerhans Cells," *Vaccine* 23:1720-29 (2005); Greenstone et al., "Chimeric Papillomavirus Virus-like Particles Elicit Antitumor Immunity Against the E7 Oncoprotein in an HPV16 Tumor Model," *Proc Natl Acad Sci USA* 95:1800-5 (1998); Rudolph et al., "Human Dendritic Cells are Activated by Chimeric Human Papillomavirus Type-16 Virus-Like Particles and Induce Epitope—Specific Human T-cell Responses in vitro," *J Immunol* 166:5917-5924 (2001); Wakabayashi, et al., "Comparison of Human Papillomavirus Type 16L1 Chimeric Virus-Like Particles Versus L1/L2 Chimeric Virus Like Particles in Tumor Prevention," *Intervirology* 45:300-307 (2002), which are hereby incorporated by reference in their entirety.

The chimeric L2 protein of the present invention is made using recombinant protein production techniques that are well known to those skilled in the art. Basically, the nucleic acid molecules encoding the various polypeptide components of a chimeric protein are ligated together along with appropriate regulatory elements that provide for expression of the chimeric protein. Typically, the nucleic acid construct encoding the chimeric protein is inserted into any of the many available expression vectors and cell systems using reagents that are well known in the art. Suitable vectors include, but are not limited to, the following viral vectors such as baculovirus lambda vector system gt1 1, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK± or KS± (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. The DNA sequences can be cloned into the vector using standard cloning procedures known in the art, including restriction enzyme cleavage and ligation with DNA ligase as described by Sambrook et al., *Molecular Cloning: A Laboratory Manual*, Second Edition, Cold Spring Harbor Press, NY (1989), and Ausubel et al., *Current Protocols in Molecular Biology*, John Wiley & Sons, New York, N.Y. (1989), which are hereby incorporated by reference in their entirety. Recombinant molecules, including plasmids, can be introduced into cells via transformation, particularly transduction, conjugation, mobilization, or electroporation. Once these recombinant plasmids are introduced into unicellular cultures, including prokaryotic organisms and eukaryotic cells, the cells are grown in tissue culture and vectors can be replicated.

For the expression of HPV L1 and L2 proteins, including chimeric L1 or L2 proteins, and VLP assembly, recombinant vectors produced above are used to infect a host cell. Any number of vector-host combinations can be employed, including yeast vectors and yeast hosts, baculovirus vectors and insect host cells, vaccinia virus vectors and mammalian host cells, etc.

The chimeric VLPs of the present invention are preferably formed in Sf-9 insect cells upon expression of the L1 and chimeric L2 proteins using recombinant baculovirus. General methods for handling and preparing baculovirus vectors and baculovirus DNA, as well as insect cell culture procedures, are outlined for example in *The Molecular Biology of Baculoviruses*, Doerffer et al., Eds. Springer-Verlag, Berlin, pages 31-49; Kool et al., *Arch. Virol.* 130: 1-16 (1993), each of which is incorporated by reference in their entirety. Purification of the VLPs can be achieved very simply by means of centrifugation in CsCl or sucrose gradients (Kimbauer et al., *Proc. Natl. Acad. Sci.* (USA) 99:12180-12814 (1992); Kirnbaurer et al., *J. Virol.* 67:6929-6936 (1994); Proso et al., *J. Virol.* 6714:1936-1944 (1992); Sasagawa et al., *Virology* 2016:126-195 (1995); Volpers et al., *J. Virol.* 69:3258-3264 (1995); Zhou et al., *J. Gen. Virol.* 74:762-769 (1993); Rose et al., "Expression of human papillomavirus type 11 L1 protein in insect cells: in vivo and in vitro assembly of viruslike particles," *J Virol.* 67(4): 1936-1944 (1993); Rose et al., "Serologic differentiation of human papillomavirus (HPV) types 11, 16, and 18 L1 virus-like particles (VLPs)," *J. Gen. Virol.*, 75:2445-2449 (1994), which are hereby incorporated by reference in their entirety).

The DNA molecule that is intended to be used in combination with the VLP or chimeric VLP is a recombinant DNA molecule encoding a second immunogenic epitope. Methods of generating recombinant DNA molecules are well known in the art as described above. To facilitate antigen presentation and further enhance the immune response of a DNA molecule, the immunogenic epitope of the present invention can be linked to Calreticulin (CRT) as described by Peng et al., "Development of a DNA Vaccine Targeting Human Papillomavirus Type 16 Oncoprotein E6," *J Virol* 78:8468-76 (2004), which is hereby incorporated by reference in its entirety. Additionally, the immunogenic epitope can be linked to *Mycobacterium tuberculosis* heat shock protein-70 (HSP70), the translocation domain of *Pseudomonas aerugenosa* exotoxin A (ETA9dII)), or the sorting signal of the lysosome-associated membrane protein-1 (LAMP-1) to enhance MHC Class I and/or II presentation (Kim et al., "Comparison of HPV DNA Vaccines Employing Intracellular Targeting Strategies," *Gene Therapy* 11:1011-1018 (2004), which is hereby incorporated by reference in its entirety).

The DNA sequence can be cloned into an expression vector using standard cloning procedures in the art, as described by Sambrook et al., *Molecular Cloning: A Laboratory Manual*, Second Edition, Cold Spring Harbor Press, NY (1989), and Ausubel et al., *Current Protocols in Molecular Biology*, John Wiley & Sons, New York, N.Y. (1989), which are hereby incorporated by reference in their entirety. Suitable vectors include those described above.

The DNA molecule can be circular, as in the form of a plasmid or expression vector. Alternatively, the DNA molecule can be linearized. The DNA molecule can be in the form of chromatin, i.e., in association with histones H1, H2a, H2b, H3, H4 or mixtures thereof, as described by PCT Application Publ. No. WO 03/018622 to Sapp, which is hereby incorporated by reference in its entirety. Alternatively, the DNA can be histone-free DNA.

The first and second epitopes of the composition of the present invention can be pathogen-specific epitopes. In a preferred embodiment, the first pathogen-specific epitope fused to the L2 protein or polypeptide of the VLP and the second pathogen-specific epitope encoded by the DNA molecule can be the same or substantially the same epitope. Alternatively, the first and second pathogen specific epitopes are different, but specific for the same pathogen. Alternatively, the first and second pathogen specific epitopes can be specific for different pathogens. In addition, more than one immunogenic epitope can be fused to the L1 or L2 protein of the VLP or be encoded by the DNA molecule.

The pathogen-specific epitope can be an epitope of a pathogen protein whose activity is required for initial pathogen infection or for maintenance of pathogen infection.

The pathogen-specific epitopes of the present invention can be derived from a bacterium, a virus, a protozoan, or a fungus.

Viral pathogens include, without limitation, the group of RNA viruses, DNA viruses, adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus such as measles virus, rubulavirus (such as mumps virus), pneumonoviridae (e.g., pneumovirus, human respiratory syncytial virus), metapneumovirus (e.g., avian pneumovirus and human metapneumovirus), picornaviridae (e.g., enterovirus, rhinovirus, hepatovirus such as human hepatitis A virus, cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (such as human immunodeficiency virus 1 and human immunodeficiency virus 2; and spumavirus), flaviviridae (e.g., hepatitis C virus), hepadnaviridae (e.g., hepatitis B virus), togaviridae (e.g., alphavirus (such as sindbis virus and rubivirus such as rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus), Cytomegalovirus (mononucleosis), Dengue virus (dengue fever, shock syndrome), Epstein-Barr virus (mononucleosis, Burkitt's lymphoma), Human T-cell lymphotropic virus type 1 (T-cell leukemia), Influenza A, B, and C (respiratory disease), Japanese encephalitis virus (pneumonia, encephalopathy), Poliovirus (paralysis), Rhinovirus (common cold), Rubella virus (fetal malformations), Vaccinia virus (generalized infection), Yellow fever virus (jaundice, renal and hepatic failure), and Varicella zoster virus (chickenpox).

Bacterial pathogens include, without limitation, *Bacillus anthracis, Bordetella pertussis, Borrelia burgdorferi, Campylobacter jejuni, Chlamydia trachomatis, Clostridium botulinum, Clostridium tetani, Corynebacterium dipththeriae, Escherichia coli*, enterohemorrhagic *E. coli*, enterotoxigenic *E. coli, Haemophilus influenzae* type B and nontypable, *Helicobacter pylori, Legionella pneumophila, Listeria monocytogenes, Mycobacterium* spp., *Mycobacterium leprae, Mycobacterium tuberculosis, Neisseria gonorrhoeae, Neisseria meningitidis, Pneumococcus* spp., *Pseudomonas aeruginosa, Rickettsia, Salmonella* spp., *Shigella* spp., *Staphylococcus* spp., *Staphylococcus aureus, Streptococcus* spp., *Streptococcus pneumoniae, Streptococcus pyogenes, Streptococcus* B, Group A beta hemolytic *Streptococcus, Streptococcus mutans, Treponema pallidum, Vibrio cholerae,* and *Yersinia pestis*.

Pathogenic fungi include, without limitation, the genera *Aspergillus* (e.g., *Aspergillus fumigates*), *Blastomyces, Candida* (e.g., *Candida albicans*), *Coccidiodes, Cryptococcus, Histoplasma, Phycomyces, Tinea corporis, Tinea unguis, Sporothrix schenckii,* and *Pneumocystis carinii*.

Pathogenic protozoan include, without limitation, *Giardia* spp. such as *Giardia lamblia*.

In another embodiment of the present invention the first and second epitopes of the composition are tumor-specific epitopes.

One preferred embodiment of the present invention relates to a composition that is effective for generating an HIV-specific immune response. The composition can contain epitopes derived from HIV early regulatory proteins including HIV Tat, Rev, and Nef proteins, or other HIV proteins such as Gag, Pol, Env, Vif, Vpr, and Vpu. Preferable epitopes of these proteins are those that are capable of generating neutralizing antibodies. Numerous HIV CTL/CD8+ and T-helper/CD4+ epitopes are known in the art (*HIV Molecular Immunology* 2006/2007, Korber, et al. (eds.), Los Alamos National Laboratory, Theoretical Biology and Biophysics, Los Alamos, N.M. (LA-UR 07-4752), which is incorporated by reference in its entirety) and are contemplated for use in compositions effective for generating an HIV-specific immune response.

An exemplary composition of the present invention for generating an HIV-specific immune response contains a papillomavirus chimeric virus-like particle assembled from HPV-16 L1 and a chimeric protein containing an HIV-16 L2 protein or polypeptide fused to the HIV Nef-V3 immunogenic epitope. The L2 protein can be either full-length or contain an N-terminal fragment. The Nef-V3 epitope is preferably the Nef protein lacking the first 19 amino acids fused to a well characterized immunodominant HIV IIIB gp120 V3 CTL epitope (RIQRGPGRAFVTIGK (SEQ ID NO:1)). The composition further contains a DNA molecule encoding a polypeptide that includes the same or substantially similar HIV Nef-V3 epitope.

The chimeric L2N-Nef-V3 amino acid sequence is set forth as SEQ ID NO: 2 as follows:

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
            35                  40                  45
```

-continued

```
Gly Ser Met Gly Val Phe Phe Gly Gly Leu Gly Ile Gly Thr Gly Ser
 50                  55                  60
Gly Thr Gly Gly Arg Thr Gly Tyr Ile Pro Leu Gly Thr Arg Pro Pro
 65                  70                  75                  80
Thr Ala Thr Asp Thr Leu Ala Pro Val Arg Pro Pro Leu Thr Val Asp
                 85                  90                  95
Pro Val Gly Pro Ser Asp Pro Ser Ile Val Ser Leu Val Glu Glu Thr
            100                 105                 110
Ser Phe Ile Asp Ala Gly Ala Pro Thr Ser Val Pro Ser Ile Pro Pro
        115                 120                 125
Asp Val Ser Gly Phe Ser Ile Thr Thr Ser Thr Asp Thr Thr Pro Ala
    130                 135                 140
Ile Leu Asp Ile Asn Asn Thr Val Thr Val Thr Thr His Asn Asn
145                 150                 155                 160
Pro Thr Phe Thr Asp Pro Ser Val Leu Gln Pro Pro Thr Pro Ala Glu
                165                 170                 175
Thr Gly Gly His Phe Thr Leu Ser Ser Ser Thr Ile Ser Thr His Asn
            180                 185                 190
Tyr Glu Glu Ile Pro Met Asp Thr Phe Ile Val Ser Thr Asn Pro Asn
        195                 200                 205
Thr Val Thr Ser Ser Thr Pro Ile Pro Gly Ser Arg Pro Val Ala Arg
    210                 215                 220
Leu Met Arg Arg Ala Glu Pro Ala Ala Glu Gly Val Gly Ala Val Ser
225                 230                 235                 240
Arg Asp Leu Glu Lys His Gly Ala Ile Thr Ser Ser Asn Thr Ala Ala
                245                 250                 255
Thr Asn Ala Ala Cys Ala Trp Leu Glu Ala Gln Glu Glu Glu Glu Val
            260                 265                 270
Gly Phe Pro Val Arg Pro Gln Val Pro Leu Arg Pro Met Thr Tyr Lys
        275                 280                 285
Ala Ala Val Asp Leu Ser His Phe Leu Lys Glu Lys Gly Gly Leu Glu
    290                 295                 300
Gly Leu Ile Tyr Ser Gln Lys Arg Gln Asp Ile Leu Asp Leu Trp Val
305                 310                 315                 320
Tyr His Thr Gln Gly Tyr Phe Pro Asp Trp Gln Asn Tyr Thr Pro Gly
                325                 330                 335
Pro Gly Ile Arg Tyr Pro Leu Thr Phe Gly Trp Cys Phe Lys Leu Val
            340                 345                 350
Pro Val Glu Pro Glu Lys Val Glu Glu Ala Asn Glu Gly Glu Asn Asn
        355                 360                 365
Cys Leu Leu His Pro Met Ser Gln His Gly Met Asp Asp Pro Glu Lys
    370                 375                 380
Glu Val Leu Val Trp Lys Phe Asp Ser Lys Leu Ala Phe His His Met
385                 390                 395                 400
Ala Arg Glu Leu His Pro Glu Tyr Tyr Lys Asp Cys Arg Ile Gln Arg
                405                 410                 415
Gly Pro Gly Arg Ala Phe Val Thr Ile Gly Lys Asp Tyr Lys Asp Asp
            420                 425                 430
Asp Asp Lys
        435
```

This chimeric L2N-Nef-V3 polypeptide is encoded by the nucleotide sequence of SEQ ID NO: 3 as follows:

```
atgcgacaca aacgttctgc aaaacgcaca aaacgtgcat cggctaccca actttataaa    60
acatgcaaac aggcaggtac atgtccacct gacattatac ctaaggttga aggcaaaact   120
attgctgaac aaatattaca atatggaagt atgggtgtat ttttggtgg gttaggaatt    180
ggaacagggt cgggtacagg cggacgcact gggtatattc cattgggaac aaggcctccc   240
acagctacag atacacttgc tcctgtaaga ccccctttaa cagtagatcc tgtgggccct   300
tctgatcctt ctatagtttc tttagtggaa gaaactagtt ttattgatgc tggtgcacca   360
acatctgtac cttccattcc cccagatgta tcaggattta gtattactac ttcaactgat   420
accacacctg ctatattaga tattaataat actgttacta ctgttactac acataataat   480
cccactttca ctgacccatc tgtattgcag cctccaacac tgcagaaaac tggagggcat   540
tttacacttt catcatccac tattagtaca cataattatg aagaaattcc tatggataca   600
tttattgtta gcacaaaccc taacacagta actagtagca cacccatacc agggtctcgc   660
ccagtggcac gcctaatgag gcgagctgag ccagcagcag agggagtggg agcagtatct   720
cgagacctgg aaaaacatgg agcaattaca agtagcaata gcagcagctac caatgctgct   780
tgtgcctggc tagaagcaca agaggaggaa gaagtgggt ttccagtcag acctcaggta    840
cctttaagac caatgactta caaggcagca gtagatctta gccactttt aaaagaaaag    900
ggggggactgg aagggttaat ttactcccaa aaaagacaag atatccttga tctgtgggtc   960
taccacacac aaggctactt ccctgattgg cagaactaca caccagggcc aggaatcaga  1020
tatccactga cctttgggtg gtgcttcaaa ctagtaccag ttgagccaga aaggtagaa   1080
gaggccaatg aaggagagaa caactgcttg ctacaccta tgagccagca tgggatggat  1140
gacccagaga agaagtatt agtgtggaag tttgacagca aactagcatt tcatcacatg  1200
gcccgagagc tgcatccgga gtactacaaa gactgccgaa tccaacgcgg accaggtcga  1260
gcatttgtaa caattggaaa agactacaag gacgacgatg acaagtag              1308
```

The chimeric L2(full)-Nef-V3 amino acid sequence is set forth as SEQ ID NO: 4 as follows:

```
Met Arg His Lys Arg Ser Ala Lys Arg Thr Lys Arg Ala Ser Ala Thr
1               5                   10                  15
Gln Leu Tyr Lys Thr Cys Lys Gln Ala Gly Thr Cys Pro Pro Asp Ile
                20                  25                  30
Ile Pro Lys Val Glu Gly Lys Thr Ile Ala Glu Gln Ile Leu Gln Tyr
            35                  40                  45
Gly Ser Met Gly Val Phe Phe Gly Gly Leu Gly Ile Gly Thr Gly Ser
        50                  55                  60
Gly Thr Gly Gly Arg Thr Gly Tyr Ile Pro Leu Gly Thr Arg Pro Pro
65                  70                  75                  80
Thr Ala Thr Asp Thr Leu Ala Pro Val Arg Pro Pro Leu Thr Val Asp
                85                  90                  95
Pro Val Gly Pro Ser Asp Pro Ser Ile Val Ser Leu Val Glu Glu Thr
            100                 105                 110
Ser Phe Ile Asp Ala Gly Ala Pro Thr Ser Val Pro Ser Ile Pro Pro
            115                 120                 125
Asp Val Ser Gly Phe Ser Ile Thr Thr Ser Thr Asp Thr Thr Pro Ala
        130                 135                 140
Ile Leu Asp Ile Asn Asn Thr Val Thr Thr Val Thr Thr His Asn Asn
```

-continued

```
            145                 150                 155                 160
Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
                180                 185                 190

Tyr Glu Glu Ile Pro Met Asp Thr Phe Ile Val Ser Thr Asn Pro Asn
                195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
                260                 265                 270

Asn Ser Ile Asn Ile Ala Pro Asp Pro Asp Phe Leu Asp Ile Val Ala
                275                 280                 285

Leu His Arg Pro Ala Leu Thr Ser Arg Arg Thr Gly Ile Arg Tyr Ser
290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asp Pro Ala
                325                 330                 335

Glu Glu Ile Glu Leu Gln Thr Ile Thr Pro Ser Thr Tyr Thr Thr
                340                 345                 350

Ser His Ala Ala Ser Pro Thr Ser Ile Asn Asn Gly Leu Tyr Asp Ile
                355                 360                 365

Tyr Ala Asp Asp Phe Ile Thr Asp Thr Ser Thr Thr Pro Val Pro Ser
    370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
                435                 440                 445

His Pro Ser Tyr Tyr Met Leu Arg Lys Arg Arg Lys Arg Leu Pro Tyr
                450                 455                 460

Phe Phe Ser Asp Val Ser Leu Ala Ala Met Arg Arg Ala Glu Pro Ala
465                 470                 475                 480

Ala Glu Gly Val Gly Ala Val Ser Arg Asp Leu Glu Lys His Gly Ala
                485                 490                 495

Ile Thr Ser Ser Asn Thr Ala Thr Asn Ala Ala Cys Ala Trp Leu
                500                 505                 510

Glu Ala Gln Glu Glu Glu Val Gly Phe Pro Val Arg Pro Gln Val
                515                 520                 525

Pro Leu Arg Pro Met Thr Tyr Lys Ala Ala Val Asp Leu Ser His Phe
                530                 535                 540

Leu Lys Glu Lys Gly Gly Leu Glu Gly Leu Ile Tyr Ser Gln Lys Arg
545                 550                 555                 560

Gln Asp Ile Leu Asp Leu Trp Val Tyr His Thr Gln Gly Tyr Phe Pro
                565                 570                 575

Asp Trp Gln Asn Tyr Thr Pro Gly Pro Gly Ile Arg Tyr Pro Leu Thr
```

```
                       580               585                 590
Phe Gly Trp Cys Phe Lys Leu Val Pro Val Glu Pro Glu Lys Val

```
caagatatcc ttgatctgtg ggtctaccac acacaaggct acttccctga ttggcagaac   1740
tacacaccag ggccaggaat cagatatcca ctgacctttg ggtggtgctt caaactagta   1800
ccagttgagc cagagaaggt agaagaggcc aatgaaggag agaacaactg cttgctacac   1860
cctatgagcc agcatgggat ggatgaccca gagaaagaag tattagtgtg gaagtttgac   1920
agcaaactag catttcatca catggcccga gagctgcatc cggagtacta caaagactgc   1980
cgaatccaac gcggaccagg tcgagcattt gtaacaattg gaaaagacta caaggacgac   2040
gatgacaagt ag                                                      2052
```

As indicated above, both of these chimeric L2 polypeptides are intended to be used in a chimeric VLP in combination with a recombinant DNA molecule encoding the CRT-NEF-V3-FLAG fusion protein. The amino acid sequence of this fusion protein is set forth as SEQ ID NO: 6 below:

```
Met Leu Leu Pro Val Pro Leu Leu Leu Gly Leu Leu Gly Leu Ala Ala
1               5                   10                  15

Ala Glu Pro Val Val Tyr Phe Lys Glu Gln Phe Leu Asp Gly Asp Gly
            20                  25                  30

Trp Thr Glu Arg Trp Ile Glu Ser Lys His Lys Ser Asp Phe Gly Lys
                35                  40                  45

Phe Val Leu Ser Ser Gly Lys Phe Tyr Gly Asp Gln Glu Lys Asp Lys
            50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Phe Thr
                85                  90                  95

Val Lys His Glu Gln Asn Ile Asp Cys Gly Gly Gly Tyr Val Lys Leu
            100                 105                 110

Phe Pro Ala Gly Leu Asp Gln Lys Asp Met His Gly Asp Ser Glu Tyr
                115                 120                 125

Asn Ile Met Phe Gly Pro Asp Ile Cys Gly Pro Gly Thr Lys Lys Val
            130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
                195                 200                 205

Lys Asp Pro Asp Ala Ser Lys Pro Glu Asp Trp Asp Glu Arg Ala Lys
            210                 215                 220
Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
                275                 280                 285

Trp Ile His Pro Glu Ile Asp Asn Pro Glu Tyr Ser Pro Asp Ala Asn
            290                 295                 300

Ile Tyr Ala Tyr Asp Ser Phe Ala Val Leu Gly Leu Asp Leu Trp Gln
305                 310                 315                 320
```

```
Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Thr
                340                 345                 350

Ala Glu Lys Gln Met Lys Asp Lys Gln Asp Glu Glu Gln Arg Leu Lys
                355                 360                 365

Glu Glu Glu Glu Lys Lys Arg Lys Glu Glu Glu Ala Glu Glu
            370                 375                 380

Asp Glu Glu Asp Lys Asp Lys Glu Asp Glu Asp Glu Glu
385                 390                 395                 400

Asp Lys Asp Glu Glu Glu Glu Ala Ala Gly Gln Ala Lys Asp
                405                 410                 415

Glu Leu Met Arg Arg Ala Glu Pro Ala Ala Glu Gly Val Gly Ala Val
                420                 425                 430

Ser Arg Asp Leu Glu Lys His Gly Ala Ile Thr Ser Ser Asn Thr Ala
                435                 440                 445

Ala Thr Asn Ala Ala Cys Ala Trp Leu Glu Ala Gln Glu Glu Glu
        450                 455                 460

Val Gly Phe Pro Val Arg Pro Gln Val Pro Leu Arg Pro Met Thr Tyr
465                 470                 475                 480

Lys Ala Ala Val Asp Leu Ser His Phe Leu Lys Glu Lys Gly Gly Leu
                485                 490                 495

Glu Gly Leu Ile Tyr Ser Gln Lys Arg Gln Asp Ile Leu Asp Leu Trp
                500                 505                 510

Val Tyr His Thr Gln Gly Tyr Phe Pro Asp Trp Gln Asn Tyr Thr Pro
                515                 520                 525

Gly Pro Gly Ile Arg Tyr Pro Leu Thr Phe Gly Trp Cys Phe Lys Leu
                530                 535                 540

Val Pro Val Glu Pro Glu Lys Val Glu Glu Ala Asn Glu Gly Glu Asn
545                 550                 555                 560

Asn Cys Leu Leu His Pro Met Ser Gln His Gly Met Asp Asp Pro Glu
                565                 570                 575

Lys Glu Val Leu Val Trp Lys Phe Asp Ser Lys Leu Ala Phe His His
                580                 585                 590

Met Ala Arg Glu Leu His Pro Glu Tyr Tyr Lys Asp Cys Arg Ile Gln
                595                 600                 605

Arg Gly Pro Gly Arg Ala Phe Val Thr Ile Gly Lys Asp Tyr Lys Asp
                610                 615                 620

Asp Asp Asp Lys
625
```

This CRT-NEF-V3-FLAG fusion protein is encoded by the nucleotide sequence of SEQ ID NO: 7 as follows:

```
atgctgctcc ctgtgccgct gctgctcggc ctgctcggcc tggccgccgc cgagcccgtc    60
gtctacttca aggagcagtt tctggacgga gatgggtgga ccgagcgctg gatcgaatcc   120
aaacacaagt ccgattttgg caaattcgtc ctcagttcgg gcaagttcta cggcgatcag   180
gagaaagata aagggctgca gaccagccag gacgcccgct tctacgccct gtcggcccga   240
ttcgagccgt tcagcaacaa gggccagcca ctggtggtgc agttcaccgt gaaacacgag   300
cagaacattg actgcggggg cggctacgtg aagctgtttc cggccggcct ggaccagaag   360
gacatgcacg gggactctga gtacaacatc atgtttggtc ctgacatctg tggccccggc   420
accaagaagg ttcacgtcat cttcaactac aagggcaaga acgtgctgat caacaaggac   480
```

```
atccgttgca aggacgacga gttcacacac ctgtacacgc tgatcgtgcg gccggacaac    540
acgtatgagg tgaagattga caacagccag gtggagtcgg gctccctgga ggatgactgg    600
gacttcctac cccccaagaa gataaaggac ccagatgcct cgaagcctga agactgggac    660
gagcgggcca agatcgacga ccccacggac tccaagcccg aggactggga caagcccgag    720
cacatccccg acccggacgc gaagaagccc gaagactggg acgaagaaat ggacggagag    780
tgggagccgc cggtgattca gaaccccgag tacaaggggtg agtggaagcc gcggcagatc   840
gacaaccccg attacaaagg cacctggatc caccccgaaa tcgacaaccc cgagtactcg    900
cccgacgcta acatctatgc ctacgacagc tttgccgtgc tgggcttgga cctctggcag    960
gtcaagtcgg gcaccatctt cgacaacttc ctcatcacca acgatgaggc gtacgcagag   1020
gagtttggca acgagacgtg gggcgtcacc aagacggccg agaagcagat gaaagacaag   1080
caggacgagg agcagcggct gaaggaggag gaggaggaga agaagcggaa ggaggaggag   1140
gaggccgagg aggacgagga ggacaaggac gacaaggagg acgaggatga ggacgaggag   1200
gacaaggacg aggaggagga ggaggcggcc gccggccagg ccaaggacga gctgatgagg   1260
cgagctgagc cagcagcaga gggagtggga gcagtatctc gagacctgga aaaacatgga   1320
gcaattacaa gtagcaatac agcagctacc aatgctgctt gtgcctggct agaagcacaa   1380
gaggaggaag aagtgggttt tccagtcaga cctcaggtac ctttaagacc aatgacttac   1440
aaggcagcag tagatcttag ccactttta aaagaaaagg ggggactgga agggttaatt   1500
tactcccaaa aaagacaaga tatccttgat ctgtgggtct accacacaca aggctacttc   1560
cctgattggc agaactacac accagggcca ggaatcagat atccactgac ctttgggtgg   1620
tgcttcaaac tagtaccagt tgagccagag aaggtagaag aggccaatga aggagagaac   1680
aactgcttgc tacaccctat gagccagcat gggatggatg acccagagaa agaagtatta   1740
gtgtggaagt ttgacagcaa actagcattt catcacatgg cccgagagct gcatccggag   1800
tactacaaag actgccgaat ccaacgcgga ccaggtcgag catttgtaac aattggaaaa   1860
gactacaagg acgacgatga caagtag                                       1887
```

As one of skill in the art will appreciate, the FLAG epitope is not required for the desired immune response and can be omitted. Likewise, the V3 epitope can be replaced with another epitope upon administration to humans.

Another embodiment of the present invention relates to a composition that is effective for generating an HPV-specific immune response. Such compositions contain epitopes derived from HPV L1, L2, E1, E2, E4, E5, E6 or E7 proteins. Preferable epitopes of these proteins are those that are capable of generating neutralizing antibodies.

An exemplary composition is one that contains a chimeric papillomavirus virus-like particle assembled from HPV-16 L1 and a chimeric protein containing an HPV-16 L2 protein or polypeptide fused to a polypeptide containing an epitope for the HPV-16 E6 protein. The composition further contains a DNA molecule encoding a polypeptide comprising the same or different HPV16 E6 epitope. Alternatively, the composition is one which contains a papillomavirus virus-like particle assembled from HPV-16 L1 and L2 proteins where the L2 protein is not a chimeric protein. The composition further contains a DNA molecule encoding a polypeptide comprising the same or different HPV 16 E6 epitope, preferably as a CRT-E6-FLAG fusion protein.

The chimeric L2N-E6 amino acid sequence is set forth as SEQ ID NO: 8 as follows:

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
```

```
                65                  70                  75                  80
Thr Ala Thr Asp Thr Leu Ala Pro Val Arg Pro Pro Leu Thr Val Asp
                    85                  90                  95
Pro Val Gly Pro Ser Asp Pro Ser Ile Val Ser Leu Val Glu Glu Thr
                100                 105                 110
Ser Phe Ile Asp Ala Gly Ala Pro Thr Ser Val Pro Ser Ile Pro Pro
            115                 120                 125
Asp Val Ser Gly Phe Ser Ile Thr Thr Ser Thr Asp Thr Thr Pro Ala
        130                 135                 140
Ile Leu Asp Ile Asn Asn Thr Val Thr Thr Val Thr Thr His Asn Asn
145                 150                 155                 160
Pro Thr Phe Thr Asp Pro Ser Val Leu Gln Pro Pro Thr Pro Ala Glu
                165                 170                 175
Thr Gly Gly His Phe Thr Leu Ser Ser Ser Thr Ile Ser Thr His Asn
            180                 185                 190
Tyr Glu Glu Ile Pro Met Asp Thr Phe Ile Val Ser Thr Asn Pro Asn
        195                 200                 205
Thr Val Thr Ser Ser Thr Pro Ile Pro Gly Ser Arg Pro Val Ala Arg
    210                 215                 220
Leu Met His Gln Lys Arg Thr Ala Met Phe Gln Asp Pro Gln Glu Arg
225                 230                 235                 240
Pro Arg Lys Leu Pro His Leu Cys Thr Glu Leu Gln Thr Thr Ile His
                245                 250                 255
Asp Ile Ile Leu Glu Cys Val Tyr Cys Lys Gln Gln Leu Leu Arg Arg
            260                 265                 270
Glu Val Tyr Asp Phe Ala Phe Arg Asp Leu Cys Ile Val Tyr Arg Asp
        275                 280                 285
Gly Asn Pro Tyr Ala Val Cys Asp Lys Cys Leu Lys Phe Tyr Ser Lys
    290                 295                 300
Ile Ser Glu Tyr Arg Tyr Tyr Cys Tyr Ser Val Tyr Gly Thr Thr Leu
305                 310                 315                 320
Glu Gln Gln Tyr Asn Lys Pro Leu Cys Asp Leu Leu Ile Arg Cys Ile
                325                 330                 335
Asn Cys Gln Lys Pro Leu Cys Pro Glu Glu Lys Gln Arg His Leu Asp
            340                 345                 350
Lys Lys Gln Arg Phe His Asn Ile Arg Gly Arg Trp Thr Gly Arg Cys
        355                 360                 365
Met Ser Cys Cys Arg Ser Ser Arg Thr Arg Arg Glu Thr Gln Leu
    370                 375                 380
```

This chimeric L2N-E6 polypeptide is encoded by the nucleotide sequence of SEQ ID NO: 9 as follows:

```
atgcgacaca aacgttctgc aaaacgcaca aaacgtgcat cggctaccca actttataaa    60
acatgcaaac aggcaggtac atgtccacct gacattatac ctaaggttga aggcaaaact   120
attgctgaac aaatattaca atatggaagt atgggtgtat ttttggtgg gttaggaatt   180
ggaacagggt cgggtacagg cggacgcact gggtatattc cattgggaac aaggcctccc   240
acagctacag atacacttgc tcctgtaaga ccccctttaa cagtagatcc tgtgggccct   300
tctgatcctt ctatagtttc tttagtggaa gaaactagtt ttattgatgc tggtgcacca   360
acatctgtac cttccattcc cccagatgta tcaggattta gtattactac ttcaactgat   420
accacacctg ctatattaga tattaataat actgttacta ctgttactac acataataat   480
```

-continued

```
cccactttca ctgacccatc tgtattgcag cctccaacac ctgcagaaac tggagggcat    540
tttacacttt catcatccac tattagtaca cataattatg aagaaattcc tatggataca    600
tttattgtta gcacaaaccc taacacagta actagtagca cacccatacc agggtctcgc    660
ccagtggcac gcctaatgca ccaaaagaga actgcaatgt tcaggaccc acaggagcga     720 cccagaaagt taccacagtt atgcacagag ctgcaaacaa ctatacatga tataatatta    780
gaatgtgtgt actgcaagca acagttactg cgacgtgagg tatatgactt tgcttttcgg    840
gatttatgca tagtatatag agatgggaat ccatatgctg tatgtgataa atgtttaaag    900
ttttattcta aaattagtga gtatagacat tattgttata gtttgtatgg aacaacatta    960
gaacagcaat acaacaaacc gttgtgtgat ttgttaatta ggtgtattaa ctgtcaaaag   1020
ccactgtgtc ctgaagaaaa gcaaagacat ctggacaaaa agcaaagatt ccataatata   1080
aggggtcggt ggaccggtcg atgtatgtct tgttgcagat catcaagaac acgtagagaa   1140
acccaactat aa                                                       1152
```

The chimeric L2(full)-E6 amino acid sequence is set forth as SEQ ID NO:10 as follows:

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
            35                  40                  45

Gly Ser Met Gly Val Phe Phe Gly Gly Leu Gly Ile Gly Thr Gly Ser
        50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
            115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
            195                 200                 205

Thr Val Thr Ser Ser Thr Pro Ile Pro Gly Ser Arg Pro Val Ala Arg
        210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270
```

```
Asn Ser Ile Asn Ile Ala Pro Asp Pro Asp Phe Leu Asp Ile Val Ala
        275                 280                 285
Leu His Arg Pro Ala Leu Thr Ser Arg Thr Gly Ile Arg Tyr Ser
        290                 295                 300
Arg Ile Gly Asn Lys Gln Thr Leu Arg Thr Arg Ser Gly Lys Ser Ile
305                 310                 315                 320
Gly Ala Lys Val His Tyr Tyr Asp Leu Ser Thr Ile Asp Pro Ala
                325                 330                 335
Glu Glu Ile Glu Leu Gln Thr Ile Thr Pro Ser Thr Tyr Thr Thr Thr
                340                 345                 350
Ser His Ala Ala Ser Pro Thr Ser Ile Asn Asn Gly Leu Tyr Asp Ile
        355                 360                 365
Tyr Ala Asp Asp Phe Ile Thr Asp Thr Ser Thr Pro Val Pro Ser
        370                 375                 380
Val Pro Ser Thr Ser Leu Ser Gly Tyr Ile Pro Ala Asn Thr Thr Ile
385                 390                 395                 400
Pro Phe Gly Gly Ala Tyr Asn Ile Pro Leu Val Ser Gly Pro Asp Ile
                405                 410                 415
Pro Ile Asn Ile Thr Asp Gln Ala Pro Ser Leu Ile Pro Ile Val Pro
                420                 425                 430
Gly Ser Pro Gln Tyr Thr Ile Ile Ala Asp Ala Gly Asp Phe Tyr Leu
        435                 440                 445
His Pro Ser Tyr Tyr Met Leu Arg Lys Arg Arg Lys Arg Leu Pro Tyr
        450                 455                 460
Phe Phe Ser Asp Val Ser Leu Ala Ala Met His Gln Lys Arg Thr Ala
465                 470                 475                 480
Met Phe Gln Asp Pro Gln Glu Arg Pro Arg Lys Leu Pro His Leu Cys
                485                 490                 495
Thr Glu Leu Gln Thr Thr Ile His Asp Ile Ile Leu Glu Cys Val Tyr
                500                 505                 510
Cys Lys Gln Gln Leu Leu Arg Arg Glu Val Tyr Asp Phe Ala Phe Arg
        515                 520                 525
Asp Leu Cys Ile Val Tyr Arg Asp Gly Asn Pro Tyr Ala Val Cys Asp
        530                 535                 540
Lys Cys Leu Lys Phe Tyr Ser Lys Ile Ser Glu Tyr Arg Tyr Tyr Cys
545                 550                 555                 560
Tyr Ser Val Tyr Gly Thr Thr Leu Glu Gln Gln Tyr Asn Lys Pro Leu
                565                 570                 575
Cys Asp Leu Leu Ile Arg Cys Ile Asn Cys Gln Lys Pro Leu Cys Pro
                580                 585                 590
Glu Glu Lys Gln Arg His Leu Asp Lys Lys Gln Arg Phe His Asn Ile
        595                 600                 605
Arg Gly Arg Trp Thr Gly Arg Cys Met Ser Cys Cys Arg Ser Ser Arg
        610                 615                 620
Thr Arg Arg Glu Thr Gln Leu
625                 630
```

This chimeric L2(full)-E6 polypeptide is encoded by the nucleotide sequence of SEQ ID NO: 11 as follows:

```
atgcgacaca aacgttctgc aaaacgcaca aaacgtgcat cggctaccca actttataaa    60
acatgcaaac aggcaggtac atgtccacct gacattatac ctaaggttga aggcaaaact   120
attgctgaac aaatattaca atatggaagt atgggtgtat tttttggtgg gttaggaatt   180
```

-continued

```
ggaacagggt cgggtacagg cggacgcact gggtatattc cattgggaac aaggcctccc    240
acagctacag atacacttgc tcctgtaaga cccccttaa cagtagatcc tgtgggccct     300
tctgatcctt ctatagtttc tttagtggaa gaaactagtt ttattgatgc tggtgcacca    360
acatctgtac cttccattcc cccagatgta tcaggattta gtattactac ttcaactgat    420
accacacctg ctatattaga tattaataat actgttacta ctgttactac acataataat    480
cccactttca ctgacccatc tgtattgcag cctccaacac ctgcagaaac tggagggcat    540
tttacacttt catcatccac tattagtaca cataattatg aagaaattcc tatggataca    600
tttattgtta gcacaaaccc taacacagta actagtagca cacccatacc agggtctcgc    660
ccagtggcac gcctaggatt atatagtcgc acaacacaac aggttaaagt tgtagaccct    720
gcttttgtaa ccactcccac taaacttatt acatatgata tcctgcata tgaaggtata    780
gatgtggata atacattata tttttctagt aatgataata gtattaatat agctccagat    840
cctgactttt tggatatagt tgctttacat aggccagcat taacctctag gcgtactggc    900
attaggtaca gtagaattgg taataaacaa acactacgta ctcgtagtgg aaaatctata    960
ggtgctaagg tacattatta ttatgattta agtactattg atcctgcaga agaaatagaa   1020
ttacaaacta taacaccttc tacatatact accacttcac atgcagcctc acctacttct   1080
attaataatg gattatatga tatttatgca gatgacttta ttacagatac ttctacaacc   1140
ccggtaccat ctgtaccctc tacatcttta tcaggttata ttcctgcaaa tacaacaatt   1200
ccttttggtg gtgcatacaa tattcctta gtatcaggtc ctgatatacc cattaatata    1260
actgaccaag ctccttcatt aattcctata gttccagggt ctccacaata tacaattatt   1320
gctgatgcag gtgacttta tttacatcct agttattaca tgttacgaaa acgacgtaaa    1380
cgtttaccat attttttttc agatgtctct ttggctgcca tgcaccaaaa gagaactgca   1440
atgtttcagg acccacagga gcgacccaga aagttaccac agttatgcac agagctgcaa   1500
acaactatac atgatataat attagaatgt gtgtactgca agcaacagtt actgcgacgt   1560
gaggtatatg actttgcttt tcgggattta tgcatagtat atagagatgg gaatccatat   1620
gctgtatgta taaatgttt aaagttttat tctaaaatta gtgagtatag acattattgt    1680
tatagtttgt atggaacaac attagaacag caatacaaca aaccgttgtg tgatttgtta   1740
attaggtgta ttaactgtca aaagccactg tgtcctgaag aaaagcaaag acatctggac   1800
aaaaagcaaa gattccataa tataaggggt cggtggaccg gtcgatgtat gtcttgttgc   1860
agatcatcaa gaacacgtag agaaacccag ctgtaa                             1896
```

As indicated above, both of these chimeric L2 polypeptides are intended to be used in a chimeric VLP in combination with a recombinant DNA molecule encoding a CRT-E6 fusion protein. The amino acid sequence of this fusion protein is set forth as SEQ ID NO:12 below:

```
Met Leu Leu Pro Val Pro Leu Leu Leu Gly Leu Leu Gly Leu Ala Ala
1               5                   10                  15

Ala Glu Pro Val Val Tyr Phe Lys Glu Gln Phe Leu Asp Gly Asp Gly
            20                  25                  30

Trp Thr Glu Arg Trp Ile Glu Ser Lys His Lys Ser Asp Phe Gly Lys
        35                  40                  45

Phe Val Leu Ser Ser Gly Lys Phe Tyr Gly Asp Gln Glu Lys Asp Lys
    50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Phe Thr
```

-continued

```
                85                  90                  95
Val Lys His Glu Gln Asn Ile Asp Cys Gly Gly Gly Tyr Val Lys Leu
                100                 105                 110

Phe Pro Ala Gly Leu Asp Gln Lys Asp Met His Gly Asp Ser Glu Tyr
                115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
                195                 200                 205

Lys Asp Pro Asp Ala Ser Lys Pro Glu Asp Trp Asp Glu Arg Ala Lys
                210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
                260                 265                 270

Gly Glu Trp Lys Pro Arg Gln Ile Asp Asn Pro Asp Tyr Lys Gly Thr
                275                 280                 285

Trp Ile His Pro Glu Ile Asp Asn Pro Glu Tyr Ser Pro Asp Ala Asn
                290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Thr
                340                 345                 350

Ala Glu Lys Gln Met Lys Asp Lys Gln Asp Glu Glu Gln Arg Leu Lys
                355                 360                 365

Glu Glu Glu Glu Lys Lys Arg Lys Glu Glu Glu Ala Glu Glu
                370                 375                 380

Asp Glu Glu Asp Lys Asp Asp Lys Glu Asp Glu Asp Glu Glu
385                 390                 395                 400

Asp Lys Asp Glu Glu Glu Glu Ala Ala Ala Gly Gln Ala Lys Asp
                405                 410                 415

Glu Leu Met His Gln Lys Arg Thr Ala Met Phe Gln Asp Pro Gln Glu
                420                 425                 430

Arg Pro Arg Lys Leu Pro His Leu Cys Thr Glu Leu Gln Thr Thr Ile
                435                 440                 445

His Asp Ile Ile Leu Glu Cys Val Tyr Cys Lys Gln Gln Leu Leu Arg
                450                 455                 460

Arg Glu Val Tyr Asp Phe Ala Phe Arg Asp Leu Cys Ile Val Tyr Arg
465                 470                 475                 480

Asp Gly Asn Pro Tyr Ala Val Cys Asp Lys Cys Leu Lys Phe Tyr Ser
                485                 490                 495

Lys Ile Ser Glu Tyr Arg Tyr Tyr Cys Tyr Ser Val Tyr Gly Thr Thr
                500                 505                 510

Leu Glu Gln Gln Tyr Asn Lys Pro Leu Cys Asp Leu Leu Ile Arg Cys
```

```
                515                 520                 525
Ile Asn Cys Gln Lys Pro Leu Cys Pro Glu Glu Lys Gln Arg His Leu
    530                 535                 540

Asp Lys Lys Gln Arg Phe His Asn Ile Arg Gly Arg Trp Thr Gly Arg
545                 550                 555                 560

Cys Met Ser Cys Cys Arg Ser Ser Arg Thr Arg Glu Thr Gln Leu
                565                 570                 575
```

This CRT-E6 fusion protein is encoded by the nucleotide sequence of SEQ ID NO: 13 as follows:

```
atgctgctcc ctgtgccgct gctgctcggc ctgctcggcc tggccgccgc cgagcccgtc    60
gtctacttca aggagcagtt tctggacgga gatgggtgga ccgagcgctg gatcgaatcc   120
aaacacaagt ccgattttgg caaattcgtc ctcagttcgg gcaagttcta cggcgatcag   180
gagaaagata aagggctgca gaccagccag gacgcccgct tctacgccct gtcggcccga   240
ttcgagccgt tcagcaacaa gggccagcca ctggtggtgc agttcaccgt gaacacgag    300 cagaacattg actgcggggg cggctacgtg aagctgtttc cggccggcct ggaccagaag   360
gacatgcacg gggactctga gtacaacatc atgtttggtc ctgacatctg tggccccggc   420
accaagaagg ttcacgtcat cttcaactac aagggcaaga acgtgctgat caacaaggac   480
atccgttgca aggacgacga gttcacacac ctgtacacgc tgatcgtgcg gccggacaac   540
acgtatgagg tgaagattga acagccag gtggagtcgg gctccctgga ggatgactgg   600
gacttcctac cccccaagaa gataaaggac ccagatgcct cgaagcctga agactgggac   660
gagcgggcca gatcgacga ccccacggac tccaagcccg aggactggga caagcccgag   720
cacatccccg acccggacgc gaagaagccc gaagactggg acgaagaaat ggacggagag   780
tgggagccgc cggtgattca gaaccccgag tacaagggtg agtggaagcc gcggcagatc   840
gacaaccccg attacaaagg cacctggatc caccccgaaa tcgacaaccc cgagtactcg   900
cccgacgcta acatctatgc ctacgacagc tttgccgtgc tgggcttgga cctctggcag   960
gtcaagtcgg gcaccatctt cgacaacttc ctcatcacca acgatgaggc gtacgcagag  1020
gagtttggca acgagacgtg gggcgtcacc aagacggccg agaagcagat gaaagacaag  1080
caggacgagg agcagcggct gaaggaggag gaggaggaga agaagcggaa ggaggaggag  1140
gaggccgagg aggacgagga ggacaaggac gacaaggagg acgaggatga ggacgaggag  1200
gacaaggacg aggaggagga ggaggcggcc gccggccagg ccaaggacga gctgatgcac  1260
caaaagagaa ctgcaatgtt tcaggaccca caggagcgac ccagaaagtt accacagtta  1320
tgcacagagc tgcaaacaac tatacatgat ataatattag aatgtgtgta ctgcaagcaa  1380
cagttactgc gacgtgaggt atatgacttt gcttttcggg atttatgcat agtatataga  1440
gatgggaatc catatgctgt atgtgataaa tgtttaaagt tttattctaa aattagtgag  1500
tatagacatt attgttatag tttgtatgga acaacattag aacagcaata caacaaaccg  1560
ttgtgtgatt tgttaattag gtgtattaac tgtcaaaagc cactgtgtcc tgaagaaaag  1620
caaagacatc tggacaaaaa gcaaagattc cataatataa ggggtcggtg gaccggtcga  1680
tgtatgtctt gttgcagatc atcaagaaca cgtagagaaa cccagctgta a           1731
```

The compositions of the present invention can also include a pharmaceutically acceptable carrier. Acceptable pharmaceutical carriers include solutions, suspensions, emulsions, excipients, powders, or stabilizers.

For example, compositions suitable for injectable use (e.g., intravenous, intra-arterial, intramuscular, etc.) may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Likewise, oral dosage formulations can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

The compositions of the present invention can also include an effective amount of an adjuvant. Suitable adjuvants include, without limitation, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as bacille Calmette-Guerin and *Carynebacterium parvum*.

The compositions of the present invention contain virus-like particles in an amount effective to induce an antibody-mediated immune response upon administration of the composition to a patient. Preferably, the virus-like particle is present in an amount ranging 1-100 µg, preferably 5-80 µg, more preferably 5-30 µg, most preferably 5-20 µg.

The compositions also contains a DNA molecule present in an amount effective to induce a cell-mediated immune response upon administration of the composition to the patient. Preferably, the DNA molecule is present in an amount ranging from 50 to 1000 µg, more preferably 100 to 750 µg.

The compositions of the present invention, as indicated above, can be used to induce an immune response against a pathogen or tumor in a patient. Thus, these aspects encompass co-administering the chimeric VLP and the DNA molecule encoding the second pathogen- or tumor-specific epitope to the patient. Administration of the composition(s) in this manner is effective to induce an immune response against the pathogen- or tumor-specific epitope (i.e., the first and/or second epitopes). The immune response generated using this method is greater than the combined individual immune responses generated by the papillomavirus VLP alone and the DNA molecule alone.

Effective amounts of the composition will depend upon the mode of administration, frequency of administration, nature of the treatment, age and condition of the individual to be treated, and the type of pharmaceutical composition used to deliver the compound. Effective levels of the composition may range from about 0.001 to about 2.5 mg/kg depending upon the clinical endpoints and toxicity thresholds. While individual doses may vary, optimal ranges of the effective amounts may be determined by one of ordinary skill in the art.

In these aspects of the present invention, it is contemplated that the patient can be any mammal, but preferably a human patient. Veterinary uses are also contemplated.

The composition can be administered by any means suitable for producing the desired immune response. Preferred delivery routes include intramuscularly, intraperitoneally, intravenously, intraarterialy, orally, topically, transdermally, intradermally, via inhalation, intranasally, and intravesical or intracavitary instillation.

Exemplary modes of administration include a delivery vehicle that includes the composition of the present invention. Such delivery vehicles can be in the form of a single-unit oral dosage. Alternatively, the delivery vehicle can be in the form of a syringe comprising an injectable dose or in the form of a transdermal patch containing a transdermally deliverable dosage.

As an alternative approach, the chimeric VLP and the DNA molecule can be administered separately. Thus, the chimeric VLP (with the pathogen or tumor-specific epitope) and the DNA molecule can be administered via different compositions, and different delivery vehicles (i.e., same or different types). Each administration can be carried out as described above, and the two administration steps can be carried out at the same time or with a delay between, as well as at substantially the same site or at anatomically distince sites. In a preferred embodiment, the first and second administering are carried out substantially simultaneously. This approach may further include repeating either administering step or both.

For prophylactic treatment against pathogen infection, it is intended that the composition(s) of the present invention can be administered prior to exposure of an individual to a pathogen and that the resulting immune response can inhibit or reduce the severity of the pathogen infection such that the pathogen can be eliminated from the individual. For therapeutic treatment of active pathogen infections, it is intended that the composition(s) of the present invention can be administered to an individual who is already exposed to the pathogen. The resulting enhanced immune response is believed to reduce the duration or severity of the existing pathogen infection, as well as minimize any harmful consequences of untreated pathogen infections. The composition(s) can also be administered with any other therapeutic anti-pathogen regimen.

For treatment of tumors, it is intended that the enhanced immune response against a tumor will either cause tumor shrinkage (including complete immune-mediated destruction of the tumor) or a reduction in the rate of tumor growth. Thus, it is intended that the compositions of the present invention can be used to treat individuals that are tumor positive or individuals that are considered to be in remission but highly susceptible to future tumor growth. The composition(s) can also be administered with any other therapeutic anti-tumor regimen.

EXAMPLES

The following examples are provided to illustrate embodiments of the present invention but they are by no means intended to limit its scope.

Materials and Methods for Examples 1-4

Animals:
Female C57BL/6 and BALB/c mice (8-10 weeks of age) were obtained from Taconic Laboratories (Germantown, N.Y.). All procedures were performed in accordance with University of Rochester approved protocols for animal use.

Plasmid DNA Constructs:
A luciferase expression construct (gWiz Luc) was obtained from Aldevron (Fargo, N. Dak.) and a green fluorescent protein (GFP) expression construct (pEGFP-$N_1$) was obtained from Clontech (Mountain View, Calif.). An HPV16 E6 expression plasmid (pcDNA3-CRTE6, kindly provided by S-W Peng and T. C Wu, Johns Hopkins University, Baltimore, Md.) was generated as previously described (Peng et al., "Development of a DNA Vaccine Targeting Human Papillomavirus Type 16 Oncoprotein E6," *J Virol* 78:8468-76 (2004), which is hereby incorporated by reference in its entirety). All plasmids were amplified in *E. coli* by standard methods, purified using an Endotoxin-free maxi prep kit (Qiagen, Valencia, Calif.), and resuspended in sterile phosphate-buffered saline (PBS; Mediatech Inc., Herndon, Va.) prior to use.

VLP Production and Purification:
Methods used for the generation of recombinant baculoviruses that mediate expression of HPV capsid proteins in insect cells have been described previously in detail (Rose et al., "Serological Differentiation of Human Papillomavirus Types 11, 16 and 18 Using Recombinant Virus-like Particles," *Journal of General Virology* 75:2445-2449 (1994) and Rose et al., "Expression of the Full-length Products of the Human Papillomavirus Type 6b (HPV-6b) and HPV-11 L2 Open Reading Frames by Recombinant Baculovirus, and Antigenic Comparisons with HPV-11 Whole Virus Particles," *Journal of General Virology* 71:2725-2729 (1990), which are hereby incorporated by reference in their entirety). *Trichoplusia ni* cells (High Five™ cells, Invitrogen, Carlsbad, Calif.) were propagated in 300-ml shake cultures in 1 L flasks (125 RPM, 27° C.) in Express Five serum-free medium (Invitrogen) and were infected at multiplicity of infection (MOI)=3. Infected cell cultures were incubated with shaking for 72 h at 27° C. Cells were pelleted (800×g) and resuspended in 20 mls of 1×PBS with Pepstatin (1 µg/ml) and Complete Protease Inhibitor cocktail (Roche Applied Science, Indianapolis, Ind.). Cells were frozen and thawed on ice and subjected to dounce homogenization (60 strokes) followed by sonication (three 30 second bursts). Sonicates were diluted in PBS and Cesium chloride (CsCl) was added to a final concentration of 0.4 g/ml. Following ultracentrifugation (100 000×g, 40 h, 4° C.), bands appearing at the buoyant density of empty capsids were removed by syringe and dialyzed against Buffer N (PBS; 0.5M NaCl). Dialysates were then subjected to sucrose sedimentation and the VLP band appearing at the 40%-60% interface was collected and subjected to two additional rounds of CsCl ultracentrifugation. Final CsCl-banded material was recovered by syringe and dialyzed against Buffer N (18 h, 4° C.) prior to storage at −80° C. VLP preparations were analyzed as previously described (Rose, R. C., "Production and Characterization of Human Papillomavirus (HPV) Virus-like Particles (VLPs): Novel Diagnostic Reagents and Vaccine Candidates for Genital HPV Disease," Doctoral Dissertation. The University of Rochester, Rochester, N.Y., USA (1994), which is hereby incorporated by reference in its entirety).

VLP-Mediated DNA Delivery In Vitro:
Using as a guide previously reported methods for VLP-mediated DNA delivery in vitro (Bousarghin et al., "Detection of Neutralizing Antibodies Against Human Papillomaviruses (HPV) by Inhibition of Gene Transfer Mediated by HPV Pseudovirions," *J Clin Microbiol* 40:926-32 (2002); Combita et al., "Gene Transfer Using Human Papillomavirus Pseudovirions Varies According to Virus Genotype and Requires Cell Surface Heparan Sulfate," *FEMS Microbiol Lett* 204:183-8 (2001), which are hereby incorporated by reference in their entirety), HEK 293T cells were seeded into 48-well plates (Costar, Corning, N.Y.) in Dulbecco's Modified Eagle's Medium (DMEM) with L-glutamine (Mediatech Inc., Herndon, Va.) supplemented with 10% fetal bovine serum (FBS), penicillin (100 IU/ml), and streptomycin (100 µg/ml). VLP-DNA complexes were generated by mixing 5 µg VLPs with 0.5 µg pEGFP-$N_1$ (Clontech, Mountain View, Calif.), and incubating at room temperature for 30 minutes. After washing cells with antibiotic-free media, VLP-DNA complexes were added to each well. Plates were incubated at 37° C. for three hours. Complete DMEM was added to each well and placed at 37° C. for 48 hours to allow time for expression of GFP, which was visualized by fluorescence microscopy.

Injection/Immunization Procedures:
Luciferase expression plasmid (gWiz Luc, Aldevron, Fargo, N. Dak.) was administered parenterally (intramuscular (i.m.) injection) with or without VLPs in sterile PBS (Mediatech Inc., Herndon, Va.). A standard injection volume (50 µl) was used for all mice. VLP-mediated DNA delivery was evaluated at several stoichiometric ratios of VLPs to DNA (i.e., 1:5, 1:25, and 1:50). For intramuscular immunizations, VLPs and plasmid DNA were mixed in a final volume of 50 µl in sterile 1×PBS. Plasmids were also prepared in sterile 1×PBS in a final volume of 50 µl. Mice were immunized by a single injection of 50 µl in the hind leg muscle. All animals received a primary injection on day 0 and a booster inoculation on day 7. For intradermal (i.d.) immunizations, VLP-DNA immunogens were mixed in a final volume of 25 µl diluted in sterile 1×PBS. Control formulation (plasmid DNA alone) was also diluted to a final volume of 25 µl in sterile 1×PBS. In experiments involving intradermal inoculation in mouse ear, mice were inoculated in both ears, and each ear received 25 µl of immunogen. As before, animals received primary injections on day 0, and booster inoculations on day 7. Formulations consisting of VLPs mixed with GFP DNA, or GFP DNA alone, were prepared by mixing and/or diluting, in sterile 1×PBS to a final volume of 25 µl. Following ear inoculation solutions were allowed to absorb for approximately 20 minutes prior to sacrifice.

Analysis of VLP-Mediated Delivery and Expression of DNA In Vivo:
In experiments involving inoculation of luciferase expression plasmid, mice were subjected to in vivo image analysis on days 1, 3, and 7 after injections. Prior to imaging, mice were anesthetized with Avertin, administered parenterally (intraperitoneal (i.p.) injection; 250 mg/kg of body weight) and then injected i.p. with 4 mg (in 150 µl volume) of luciferase substrate (D-luciferin; Xenogen Corp., Alameda, Calif.). Mouse tails were marked with a non-hazardous marker to facilitate tracking animals throughout the time course of the experiment. Images were acquired using system designed for this purpose (In Vivo Imaging System (IVIS) 100; Xenogen Corp.) and analyzed with proprietary software (LivingImage, v2.11; Xenogen Corp.). Two exposure times were obtained for each group. Analyses were performed using region-of-interest on the leg, and results are plotted as photon flux (photons/s/cm$^2$/sr).

Recovery and Analysis of Migratory Cells:

Following administration of VLP-GFP plasmid complexes (or GFP plasmid alone) ears were removed, split, and maintained in culture medium as previously described (Larsen et al., "Migration and Maturation of Langerhans Cells in Skin Transplants and Explants," *J Exp Med* 172:1483-93 (1990), which is hereby incorporated by reference in its entirety). After 24 hours, non-adherent cells were collected, washed with PBS, and stained with 2 µg/ml anti-CD45-APC (clone 30-F11; BD Pharmingen, CA) and anti-MHC Class II-PE (clone M5/114.15.2; BD Pharmingen, CA) for 30 minutes at 4° C.

IFN-γ ELISpot:

Spleen and/or draining lymph nodes were harvested 7 days after booster inoculations, and single-cell suspensions were prepared (70 µm cell strainer, BD Biosciences, Inc., Bedford, Mass.) and used in IFN-γ ELISpot assay. Plates (Multiscreen-IP; Millipore Corp., Bedford, Mass.) were coated overnight at 4° C. with capture antibody (AN-18; 4 µg/ml; eBioscience, San Diego, Calif.) in 50 µl of 1×PBS. Plates were then washed with 1×PBS and blocked with IMDM Media (Invitrogen) containing 10% fetal bovine serum (Hyclone, Logan, Utah) for 2 hours at room temperature. Plates were again washed with PBS, and single cell suspensions were added, with or without E6 peptide (E6$_{48-57}$ (Peng et al., "Development of a DNA Vaccine Targeting Human Papillomavirus Type 16 Oncoprotein E6," *J Virol* 78:8468-76 (2004), which is hereby incorporated by reference in its entirety)), overnight at 37° C. Plates were washed once with PBS and again with PBS-T (PBS with 0.05% Tween-20). Biotinylated detection antibody (R4-A62; eBioscience, Inc., San Diego, Calif.) was added and plates were incubated for a period of 2 hours at room temperature. Plates were then washed with PBS-T, Streptavidin-alkaline phosphatase (KPL, Gaithersburg, Md.) was added, and plates were incubated 1 hour at room temperature, washed with PBS-T, developed with alkaline phosphatase substrate following manufacture's protocol (Vector Labs, Burlingame, Calif.), and analyzed (ImmunoSpot analyzer and software; Cellular Technologies, Ltd., Cleveland, Ohio). Results are graphed as spots per million splenocytes.

Example 1

VLP-Mediated DNA Delivery In Vitro

Figure 1B:
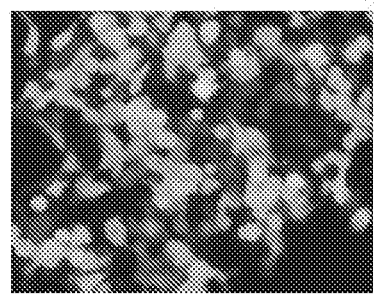
Figure 1C:
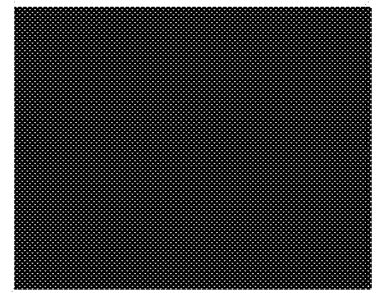
Figure 1D:
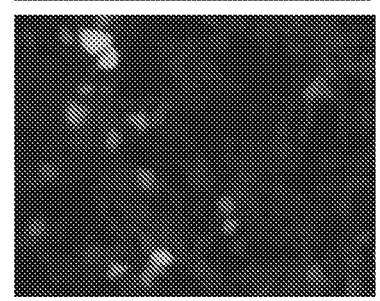
Figure 1E:

To assess the relative importance of the L2 minor capsid protein for gene delivery in vitro, a GFP reporter construct (pEGFP-N$_1$ plasmid DNA) in combination with VLPs that consisted either of HPV16 L1 alone (L1 VLPs), HPV16 L1 with HPV16 L2 (L1/L2 VLPs), or HPV16 L1/L2 VLPs in which the L2 protein was truncated (i.e., consisting of L2 amino-terminal residues 1-225, and denoted as "L2N") were used. Accordingly, L2N lacks the recently described 23 amino acid membrane-destabilizing L2 peptide sequence (Kamper et al., "A Membrane-destabilizing Peptide in Capsid Protein L2 is Required for Egress of Papillomavirus Genomes from Endosomes," *J Virol* 80:759-68 (2006), which is hereby incorporated by reference in its entirety) located near the L2 carboxyl terminus. In these experiments HEK 293T cells were incubated with GFP DNA alone, GFP DNA formulated with Lipofectamine 2000 (Invitrogen, Carlsbad, Calif.), or GFP DNA formulated with L1 VLPs, L1/L2 VLPs, or L1/L2N VLPs. GFP expression was evaluated by fluorescence microscopy 48 hours after formulations were applied to cells. In these experiments, GFP fluorescence was not observed in cells that received plasmid alone (i.e., in the absence of transfection reagent) (FIG. 1A), or plasmid co-administered with VLPs consisting of L1 alone (FIG. 1C) or L1 plus truncated L2 (L2N) (FIG. 1E). By contrast, cells transfected with GFP plasmid in combination with a standard transfection reagent (Lipofectamine 2000) (FIG. 1B) or with plasmid in combination with L1/L2 VLPs (FIG. 1D) exhibited strong GFP fluorescence. These results are consistent with data reported recently by Kamper et al. (Kamper et al., "A Membrane-destabilizing Peptide in Capsid Protein L2 is Required for Egress of Papillomavirus Genomes from Endosomes," *J Virol* 80:759-68 (2006), which is hereby incorporated by reference in its entirety), who demonstrated an association between an L2 carboxyl-terminal 23 amino acid peptide sequence and endosomal escape of co-administered plasmid DNA. Thus, under the conditions of this assay, VLP-mediated delivery and expression of GFP plasmid in vitro was observed only in cells that received plasmid co-administered with VLPs that contained full-length L2 as shown in FIGS. 1C-E.

Example 2

VLP-Mediated DNA Delivery In Vivo

Figure 2:
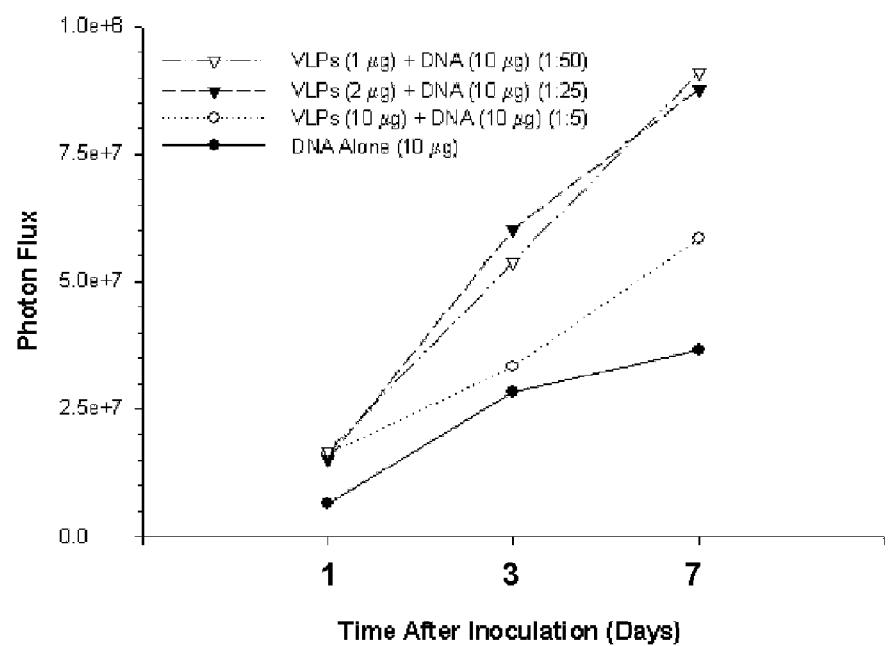
FIG. 2 is a graph showing VLP-mediated gene delivery in vivo. Mice (N=4/group) were inoculated by parenteral (intramuscular) injection with luciferase DNA (10 μg) alone (solid line) or in combination with HPV L1/L2 VLPs at three stoichiometric ratios (VLP:DNA, 1:5, 1:25, or 1:50), as indicated. Data represent group mean photon flux values obtained over a period of 7 days following injections. Optimal enhancement of plasmid DNA delivery was observed at a VLP:DNA ratio of 1:25.

To examine VLP-mediated gene delivery in living mice, a luciferase reporter construct (gWIZLuc, Aldevron, Fargo, N. Dak.) was employed along with an imaging system that permits assessment of plasmid-mediated luciferase expression in vivo (IVIS 100, Xenogen Corp., Alameda, Calif.). In these experiments, mice (N=4/group) were inoculated with luciferase plasmid alone or in combination with L1/L2 VLPs. BALB/c mice were immunized by parenteral (i.m.) injection in thigh muscle with formulations consisting of plasmid alone, VLPs alone, or plasmid in combination with VLPs, as indicated in FIG. 2. In vivo image analysis was performed on days 1, 3, and 7 after inoculation. Luciferase expression was detected at sites of injection 24 hours after injection in all mice that received DNA (FIG. 2), and was not observed in mice that received VLPs alone. Luciferase expression levels are represented as the magnitude of luciferase activity over time in photon flux (photons/s/cm$^2$/sr). In an effort to identify an optimal stoichiometric ratio of VLPs to DNA, three VLP:DNA ratios (1:1, 1:5, and 1:25) were evaluated, and it was determined that maximal enhancement (~3-fold over plasmid alone) of luciferase activity occurred at a ratio of 1:25.

Example 3

Figure 3:
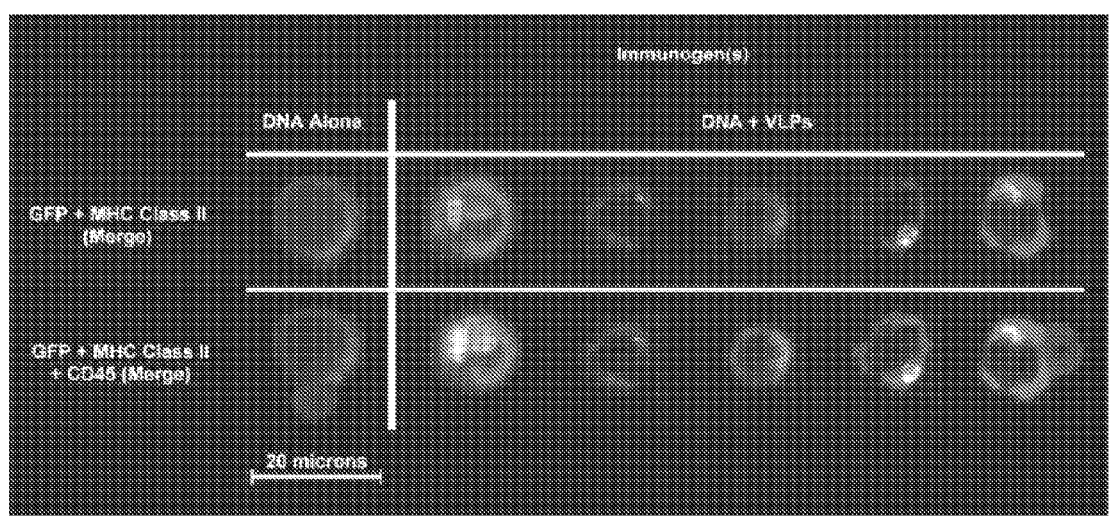
FIG. 3 depicts VLP-mediated enhancement of plasmid expression in antigen presenting cells in vivo. Mice were injected intradermally (i.d.) in ear with HPV16 L1/L2 VLPs with or without GFP plasmid DNA. Solution was allowed to absorb, ears were removed and split, and ear halves were maintained in culture medium for 24 hours to allow time for collection of migratory cells. Migrating cells were stained with anti-MHC Class II-Phycoerythrin (PE) and anti-CD45-Allophyocyanin to identify antigen presenting cells (APCs) (positive for both CD45 and MHC class II). GFP expression was visualized only in cells recovered from ears inoculated with GFP plasmid DNA in combination with L1/L2 VLPs. Figures are representative of three separate experiments.

L1/L2 VLPs Facilitate Delivery and Expression of Plasmid-Encoded GFP in Antigen Presenting Cells (APC) in vivo The previously demonstrated ability of VLPs to activate antigen-presenting cells (APC) in vitro (Fausch et al., "Heterologous Papillomavirus Virus-like Particles and Human Papillomavirus Virus-like Particle Immune Complexes Activate Human Langerhans Cells," *Vaccine* 23:1720-9 (2005); Lenz et al., "Papillomavirus-like Particles Induce Acute Activation of Dendritic Cells," *J Immunol* 166:5346-55 (2001), which are hereby incorporated by reference in their entirety) represents a potentially attractive property of this immunogen for vaccine purposes. To test in vivo the ability of VLPs to facilitate delivery and expression of plasmid DNA to APC, a GFP expression construct (pEGFP-N; Clontech, Mountain View, Calif.) was co-administered with L1/L2 VLPs by intradermal (i.d.) inoculation in mouse ear. Following administration of plasmid with or without VLPs, ears were split and examined by fluorescence microscopy to identify GFP-expressing cells. In these experiments, the ear was chosen as a site of inoculation based on previous findings that inoculation in thigh muscle limits the ability to accurately identify individual target cells. By contrast, ear inoculation readily permits visualization of GFP expression in individual cells in situ, and furthermore permits collection and evaluation of cells that migrate upon activation (Larsen et al., "Langerhans Cells Migrate Out of Skin Grafts and Cultured Skin: A Model in Which to Study the Mediators of Dendritic Leukocyte Migration," *Transplant Proc* 23:117-9 (1991); Larsen et al., "Migration and Maturation of Langerhans Cells in Skin Transplants and Explants," *J Exp Med* 172:1483-93 (1990), which are hereby incorporated by reference in their entirety). Here, mice were inoculated by intradermal (i.d.) injection, and after allowing time for cellular uptake (~20 minutes) mice were sacrificed, ears were removed and split, and ear halves were maintained in culture medium (RPMI 1640 supplemented with penicillin (50 IU/ml), streptomycin (50 μg/ml), and 10% fetal calf serum) at 37° C. for 24 hours. Following this, ear halves were removed and migrating cells were collected by centrifugation (1,000×g; 10 minutes) and stained with anti-CD45-APC and anti-MHC Class II-PE antibodies. Interestingly, although CD45$^-$/MHC Class II$^+$ migrating cells were recovered from both treatment groups, GFP expression was observed only in cells recovered from mice that received DNA in combination with L1/L2 VLPs as shown in FIG. 3. Multiple repetitions of this experiment consistently yielded the same result (FIG. 3). Thus, co-administration of L1/L2 VLPs was associated with enhanced expression of plasmid DNA in APC, a critically important component of the immune system.

Example 4

L1/L2 VLPs Strongly Enhance in vivo Immunogenicity of Plasmid-Encoded HPV16 E6 Oncoprotein Results thus far, considered together with clinical evidence of a potential therapeutic benefit of HPV E6-specific cellular immune responses (Nakagawa et al., "Persistence of Human Papillomavirus Type 16 Infection is Associated with Lack of Cytotoxic T Lymphocyte Response to the E6 Antigens," *J Infect Dis* 182:595-8 (2000), which is hereby incorporated by reference in its entirety), led to the investigation as to whether co-administration of L1/L2 VLPs could enhance immunogenicity of a plasmid designed to express the HPV 16 E6 oncoprotein. The pcDNA/CRT-E6 plasmid, which mediates expression of E6 fused at the carboxyl-terminus of rabbit Calreticulin (CRT) was previously described by Peng et al., "Development of a DNA Vaccine Targeting Human Papillomavirus Type 16 Oncoprotein E6," *J Virol* 78:8468-76 (2004), which is hereby incorporated by reference in its entirety.

Figure 4:
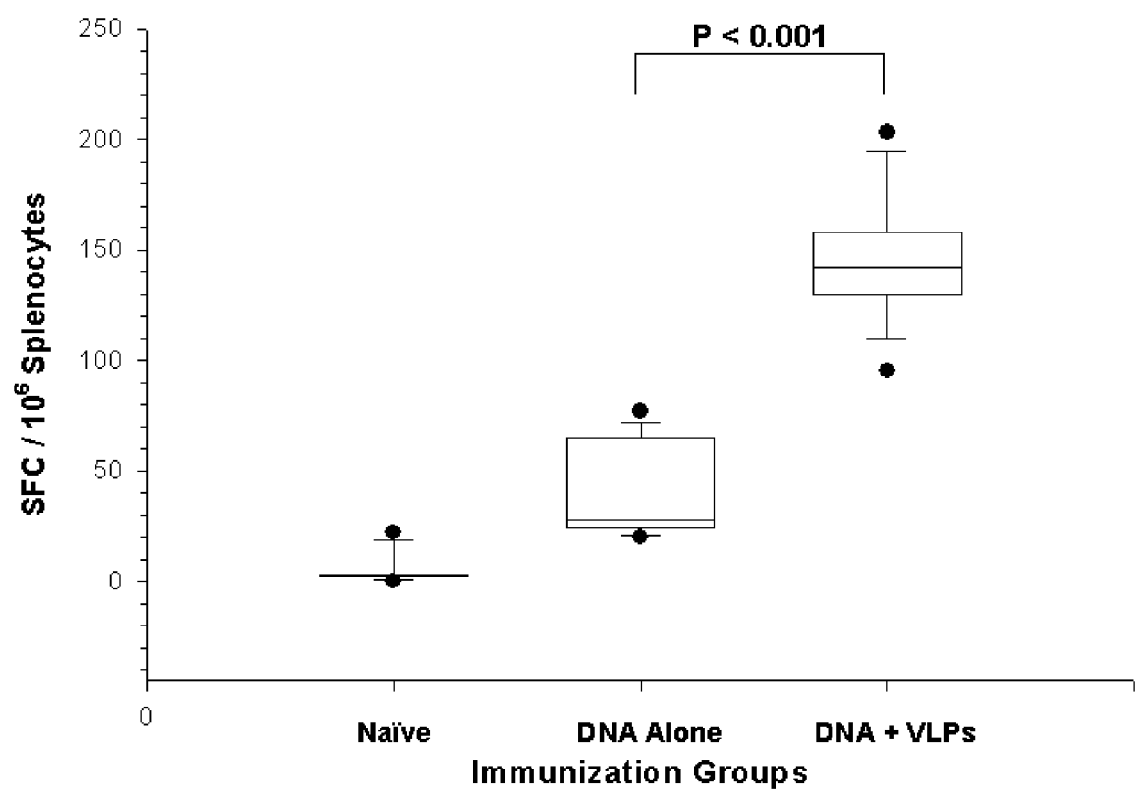
FIG. 4 is a graph depicting VLP-mediated enhancement of plasmid-encoded HPV16 E6 responses in vivo. C57BL/6 mice (N=10/group) were immunized on day 0 and boosted on day 7 as follows: (A) Control (naïve) animals; (B) pcDNA/CRT-E6 plasmid alone; (C) pcDNA/CRT-E6 plasmid in combination with HPV16 L1/L2 VLPs. Splenic E6-specific cellular immune responses were evaluated on day 14 by IFN-γ ELISpot assay. Data are presented as the mean±SEM number of IFN-γ spot forming cells (SFCs) per $1\times10^6$ splenocytes.
Figure 5:
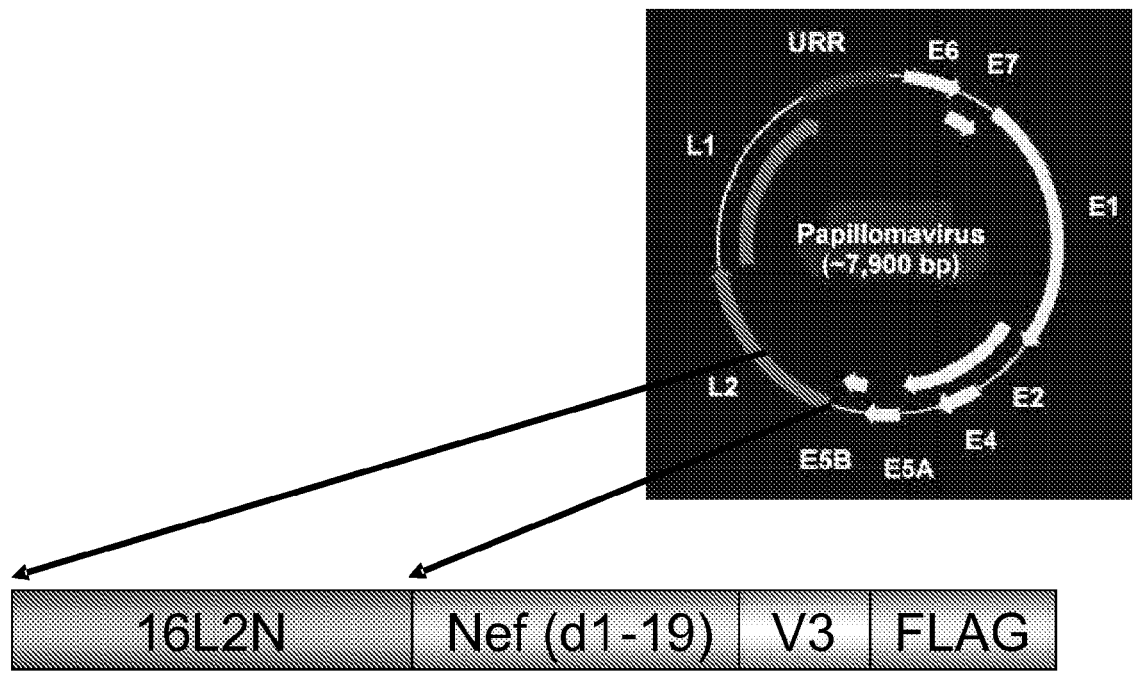
FIG. 5 is a schematic diagram of the HPV/HIV chimeric VLP (cVLP) construct. The construct contains the HIV Nef DNA sequence lacking the 19 N-terminal amino acids, Nef (d1-19), including the myristoylation site which abrogates Nef-mediated down regulation of CD4 and MHC-1 surface expression. A well characterized immunodominant HIV-1 IIIB gp120 V3 CTL epitope (RIQRGPGRAFVTIGK SEQ ID NO:1), recognized in BALB/c (H-2Dd) mice, was fused at the C-terminus of HIV-Nef coding sequence. To provide for detection of the recombinant fusion protein by Western blot immunoassay, the FLAG epitope was fused at the C-terminal end following the V3 peptide sequence.
Figure 6:
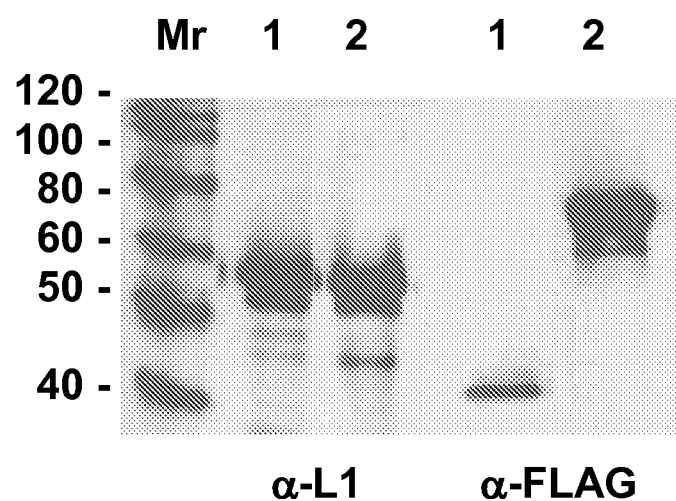
FIG. 6 shows a Western blot analysis of HPV/HIV cVLPs. The presence of 16L2N-Flag (Lane 1) protein and 16L2N-NefV3-Flag (Lane 2) fusion protein in 16L1 VLPs was verified via Western blot analyses with anti-L1 and anti-Flag antibodies.
Figure 7:
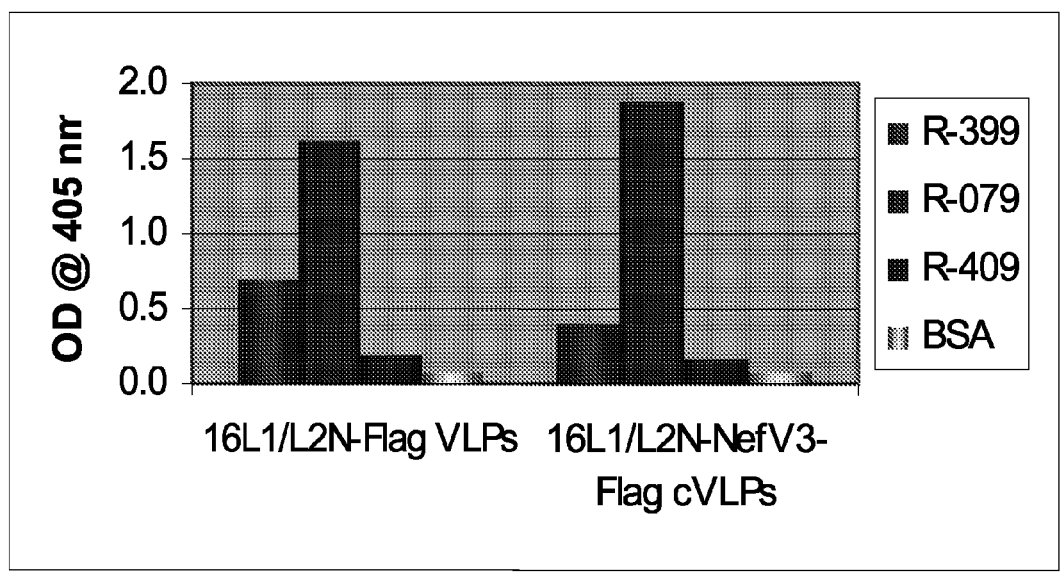
FIG. 7 is a graph illustrating an ELISA analysis of HPV/HIV cVLPs. Antibodies specific to HPV 11L1 VLPs (R-399), HPV 16L1 VLPs (R-079), and denatured HPV L1 VLPs (R-409) were tested. The HPV/HIV cVLPs exhibited minimal cross reactivity with the R-399 antibody and strong reactivity with R-079, indicating that the cVLPs retain genotype-specificity. In addition, the cVLPs exhibited no reactivity with the R-409 antibody specific for the denatured L1 protein, suggesting that the cVLPs are conformationally correct. This data indicates that the incorporation of the 16L2N-NefV3-Flag fusion protein did not interfere with VLP formation.
Figure 8:
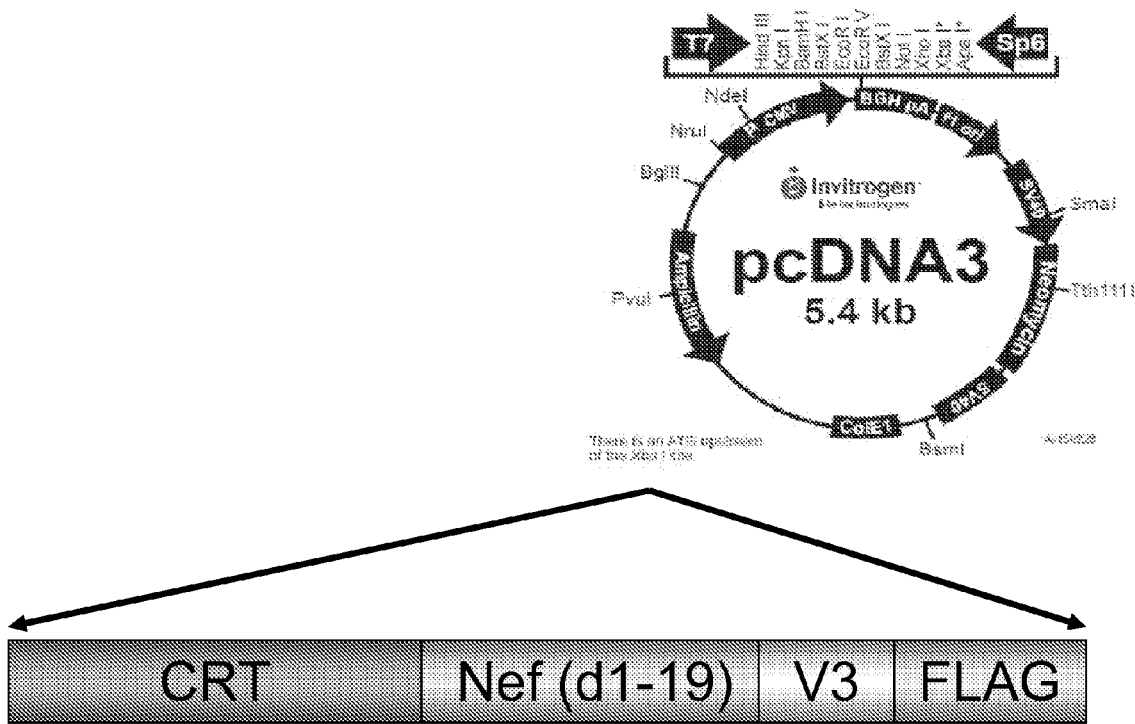
FIG. 8 is a schematic diagram of the HIV Nef-V3 expression plasmid, pcDNA3-CRT-Nef-V3-Flag. The HIV Nef(d1-19) coding sequence fused to the HIV Gag V3 cytotoxic T-lymphocyte (CTL) epitope and Flag epitope was fused to the C-terminus of Calreticulin (CRT).

In these experiments, mice (N=10/group) were inoculated by alternate routes of administration (i.d. in ear or i.m. in thigh muscle). Primary and booster inoculations were administered with DNA either alone or in combination with VLPs at a ratio of 1:25. pcDNA/CRT-E6 previously was found to elicit robust E6-specific cellular immune responses in mice when administered by gene gun (Peng et al., "Development of a DNA Vaccine Targeting Human Papillomavirus Type 16 Oncoprotein E6," *J Virol* 78:8468-76 (2004), which is hereby incorporated by reference in its entirety). Here pcDNA/CRT-E6 immunogenicity was evaluated following parenteral (i.m.) administration, with or without L1/L2 VLPs. Results obtained by IFN-γ ELISpot indicated that E6-specific cellular immune responses were enhanced approximately three-fold by co-administration of pcDNA/CRT-E6 with VLPs (P<0.001; FIG. 4).

Discussion of Examples 1-4

This work describes the capacity of VLPs to facilitate plasmid DNA delivery and expression in vitro and in vivo. Initial efforts to examine this property in vitro revealed that the presence of full-length L2 protein within VLPs was required for optimal expression of co-administered DNA. Although others have shown previously that Py VP1 VLPs (Krauzewicz et al., "Sustained Ex Vivo and In Vivo Transfer of a Reporter Gene Using Polyoma Virus Pseudocapsids," *Gene Ther* 7:1094-102 (2000) and Krauzewicz et al., "Virus-like Gene Transfer into Cells Mediated by Polyoma Virus Pseudocapsids," *Gene Ther* 7:2122-31 (2000), which are hereby incorporated by reference in their entirety), or HPV L1 VLPs (Combita et al., "Gene Transfer Using Human Papillomavirus Pseudovirions Varies According to Virus Genotype and Requires Cell Surface Heparan Sulfate," *FEMS Microbiol Lett* 204:183-8 (2001) and Touze et al., "In Vitro Gene Transfer Using Human Papillomavirus-like Particles," *Nucleic Acids Research* 26:1317-1323 (1998), which are hereby incorporated by reference in their entirety), are able to mediate delivery and expression of plasmid DNA in vitro, under the conditions described above, optimal delivery and expression of plasmid DNA occurred only in the presence of full-length L2 (See FIG. 1). The present results are consistent with results from two recent studies (Bishop et al., "Role for Centromeric Heterochromatin and PML Nuclear Bodies in the Cellular Response to Foreign DNA," *Mol Cell Biol* 26:2583-94 (2006) and Kamper et al., "A Membrane-Destabilizing Peptide in Capsid Protein L2 is Required for Egress of Papillomavirus Genomes from Endosomes," *J Virol* 80:759-68 (2006), which are hereby incorporated by reference in their entirety), and thus support the concept that L2 plays a critical role in DNA delivery and expression. In the study by Kamper et al. (Kamper et al., "A Membrane-destabilizing Peptide in Capsid Protein L2 is Required for Egress of Papillomavirus Genomes from Endosomes," *J Virol* 80:759-68 (2006), which is hereby incorporated by reference in its entirety), full-length L2 protein was found to facilitate DNA escape from endosomes, whereas in the absence of L2, or in the presence of L2 lacking a carboxyl-terminal 23 amino acid sequence, DNA was retained in the endosomal compartment. L2 has also been shown to mediate co-localization of L1 and DNA within the nucleus in promyelocytic leukemia oncogenic domains (POD), otherwise known as ND10 (Day et al., "Establishment of Papillomavirus Infection is Enhanced by Promyelocytic Leukemia Protein (PML) Expression," *Proc Natl Acad Sci USA* 101:14252-7 (2004), which is hereby incorporated by reference in its entirety). Although ND10 function is not yet fully characterized, a role in RNA processing has been suggested. In cells in $G_1$ phase of the cell cycle, it was shown, for example, that ND10 frequently are associated with nascent RNA (Kiesslich et al., "Cell Cycle-dependent Association of PML Bodies with Sites of Active Transcription in Nuclei of Mammalian Cells," *J Struct Biol* 140:167-79 (2002), which is hereby incorporated by reference in its entirety). ND10 sites are also known to contain RNA polymerase II, and CBP, a transcriptional coactivator, which supports a transcriptional role for these structures (Kiesslich et al., "Cell Cycle-Dependent Association of PML Bodies with Sites of Active Transcription in Nuclei of Mammalian Cells," *J Struct Biol* 140:167-79 (2002), which is hereby incorporated by reference in its entirety). Thus, L2 may facilitate expression of co-delivered DNA not only by mediating endosomal escape, but also by mediating localization of DNA to sites that support transcription.

Major barriers to DNA-based immunization strategies include inefficiency of target cell transduction in vivo, and inefficient expression of DNA following transduction. In the present study two model systems to examine VLP-mediated DNA delivery in vivo were employed. Using an in vivo imaging system (IVIS) designed for this purpose luciferase reporter gene expression in living mice was evaluated. Results suggested that co-administration of L1/L2 VLPs led to enhanced luciferase activity. Results initially obtained after intradermal inoculation of a GFP reporter construct in mouse ear, with or without VLPs, suggested that co-administration of VLPs exerted only a minor effect on overall GFP expression. However, when migrating APCs recovered following these inoculations were examined by immunofluorescence microscopy, GFP-expressing MHC Class II-positive cells were consistently recovered from mice inoculated with plasmid in combination with VLPs, whereas GFP expression was never observed in MHC Class II-positive cells recovered from mice that received plasmid alone. The very high reproducibility of these observations supports the conclusion that transduction of APC by plasmid DNA alone is a relatively inefficient process that can be enhanced significantly by co-administration of VLPs.

Following the finding that VLPs facilitate DNA transduction of APC in vivo, direct evidence of this effect using a plasmid designed to express a model immunogen, HPV16 E6 oncoprotein was obtained. Consistent with the initial findings described above, co-administration of L1/L2 VLPs with pcDNA-CRT/E6 expression plasmid was associated with significant enhancement of E6-specific cellular immune responses (P<0.001; FIG. 4).

In conclusion, full-length L2 protein is required for optimal delivery and expression of DNA in vitro, use of L1/L2 VLPs is associated with functional delivery of DNA to APC in vivo, and in vivo co-administration of VLPs is also associated with significant enhancement of immunogenicity of a DNA-encoded antigen in vivo. These findings support the development of VLP-based strategies for combined prophylaxis and therapy of HPV-associated diseases, and for using VLPs in an effort to circumvent barriers commonly encountered with DNA-based immunization strategies.

Materials and Methods for Example 5

Animals:

Female BALB/c mice and C57BL/6 mice (6-10 weeks of age) were obtained from Taconic Laboratories (Germantown, N.Y.). All procedures were performed in accordance with animal use protocols approved by University Committee on Animal Resources (UCAR) at the University of Rochester.

Plasmids DNA Construct:

The plasmid DNA construct for mice immunizations, expressing HIV-1 Nef polypeptide, was generated by cloning genes into pcDNA3 vector (Invitrogen, Carlsbad, Calif.). Nef gene lacking the first 19 amino acids was amplified by PCR from a plasmid containing an artificially generated Nef consensus sequence constructed from 54 HIV-1 patient isolates (AIDS Research and Reference Reagent Program, Division of AIDS, NIAID, NIH: from Dr. Ron Swanstrom). A reverse primer with sequences encoding for RIQRGPGRAFVTIGK (SEQ ID NO:1) amino acid sequence (denoted as V3) and FLAG tag was used to amplify Nef gene. The resulting NefV3-Flag DNA fragment was cloned into pcDNA3 plasmid at the C-terminus of rabbit calreticulin (CRT) gene. The pcDNA3-CRT-NefV3-Flag plasmid construct was sequenced (SEQ ID NO:7) and the expression of CRT-NefV3-Flag fusion protein (SEQ ID NO:6) was verified in the mammalian cell transfection experiment using HEK 293T cells by Western blot analyses. DNA plasmid for mice immunizations were amplified in *E. coli* by standard methods, purified using an Endotoxin-Free Mega Prep Kit (Qiagen, Valencia, Calif.), and resuspended in sterile PBS.

Generation of Recombinant Baculoviruses:

Recombinant baculoviruses were generated by co-transfection of *Spodoptera frugiperda* (Sf-9) cells (ATCC) with mixture of linearized wild-type AcNPV baculovirus DNA (Baculogold™, Pharmingen, Carlsbad, Calif.) and recombinant transfer vector plasmid DNA via cellfectin technique. Homologous recombination occurred in the insect cells, resulting in the generation of recombinant baculoviruses expressing the HPV/HIV fusion proteins. After incubation at 28° C. for 72 hours, cell culture supernatants containing recombinant baculoviruses were passaged a few times in fresh Sf-9 cells to obtain a high-titer recombinant baculovirus inoculum. Recombinant baculoviruses expressing high levels of HPV/HIV fusion proteins were confirmed by Western blot analyses.

VLP Production and Purification:

*Trichoplusia ni* (*T. ni*) cells (High Five™ cells, Invitrogen, Carlsbad, Calif.) were propagated in 300 ml shake cultures in 1 L flasks. At the optimum cells density, insect cells were co-infected with recombinant baculovirus expressing HPV/HIV fusion protein (L2N-Nef-V3, SEQ ID NO:3 or L2(full)-Nef-V3, SEQ ID NO:5) and HPV 16L1 baculovirus, and incubated at 27° C. for 72 h with shaking (125 rpm). Infected cells were pelleted and resuspended in 20 ml of PBS with Pepstatin (1 µg/ml) and Complete Protease Inhibitor Cocktail (Roche Applied Science, Indianapolis, Ind.), frozen at −80° C. Cells were thawed on ice and subjected to dounce homogenization, followed by sonication. Cell lysates were diluted in PBS and 80% cesium chloride (CsCl) was added to the final concentration of 40% CsCl (0.4 g/ml). Following the ultracentrifugation (28,000 rpm, 40 h, 4° C.), bands present at the buoyant density of capsids were removed by syringe and dialyzed against Buffer N (PBS with 0.5M NaCl). After the sucrose gradient sedimentation of the dialysates, the VLP band appearing at the 40-60% interface was collected and put through two additional rounds of CsCl ultracentrifugation. Final CsCl-banded VLP materials were collected by syringe and dialyzed against Buffer N prior to storage at −80° C. Purified HPV/HIV cVLPs were characterized by Western blot and ELISA immunoassays. The purity and morphology of HPV/HIV cVLPs were evaluated by SDS-PAGE/Coomassie gel staining and electron microscopy, respectively.

Figure 9:
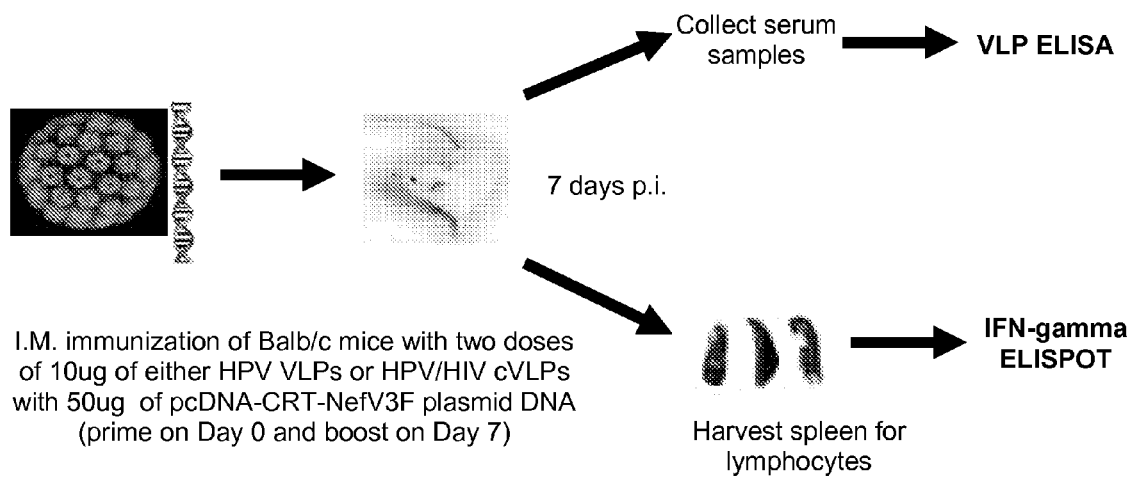
FIG. 9 illustrates the HPV/HIV cVLP/DNA co-administration strategy.

Immunization Procedure:

For all immunizations, HPV/HIV cVLPs and plasmid DNA were either diluted or mixed in sterile PBS. Mice were immunized by a single injection in the hind leg muscle. All mice received a primary inoculation on day 0 and a booster inoculation on day 7 (FIG. 9). In some experiments, mice were given intraperitoneal injection in comparison with intramuscular administration of immunogens.

IFN-γ ELISpot:

Spleens from mice were harvested and made into single cell suspensions by filtering through a 70 µm cell strainer (BD Biosciences, Inc., Bedford, Mass.). Splenocytes were resuspended in Iscove's Modified Dulbecco's Medium (IMDM; Invitrogen, Carlsbad, Calif.) supplemented with 10% fetal bovine serum (Hyclone, Logan, Utah), 1% PenStrep (Invitrogen, Carlsbad, Calif.), and 2 IU/ml IL-2. The wells of 96-well nitrocellulose plates (Multiscreen-IP; Millipore Corp., Bedford, Mass.) were treated with 70% ethanol and washed with PBS. The plates were coated with 4 µg/ml of anti-mouse IFN-γ mAb (AN-18; eBioscience, San Diego, Calif.) in PBS overnight at 4° C. Plates were then washed with PBS and blocked with Iscove's Modified Dulbecco's Medium (IMDM; Invitrogen, Carlsbad, Calif.) containing 10% fetal bovine serum (Hyclone, Logan, Utah) for at least 2 h at room temperature. Plates were washed and single cell suspensions were added in various concentrations, with or without peptide, and incubated for 18-20 h at 37° C. with 5% $CO_2$. Plates were washed many times with PBS and then with PBS-T (PBS with 0.05% Tween-20). Biotinylated IFN-γ detection antibody (R4-A62; eBioscience, San Diego, Calif.) was added and plates were incubated overnight at 4° C. Plates were then washed with PBS-T and streptavidin-alkaline phosphatase (Strep-AP; KPL, Gaithersburg, Md.) was added and incubated for 1 h at room temperature. Then plates were washed with PBS-T and alkaline phosphtase substrate was added following the manufacture's protocol (Vector Labs, Burlingame, Calif.). The plates were washed with tap water when spots were visualized and were analyzed using ImmunoSpot analyzer and software (Cellular Technologies Ltd., Cleveland, Ohio). Results were graphed as spot forming cells (SFCs) per million splenocytes.

Statistical Analyses:

Prism-4 software was used for the data analyses and graphics. Statistical analyses were performed using the Mann-Whitney non-parametric test, and statistical significance was set at $p<0.05$.

Example 5

Figure 10:
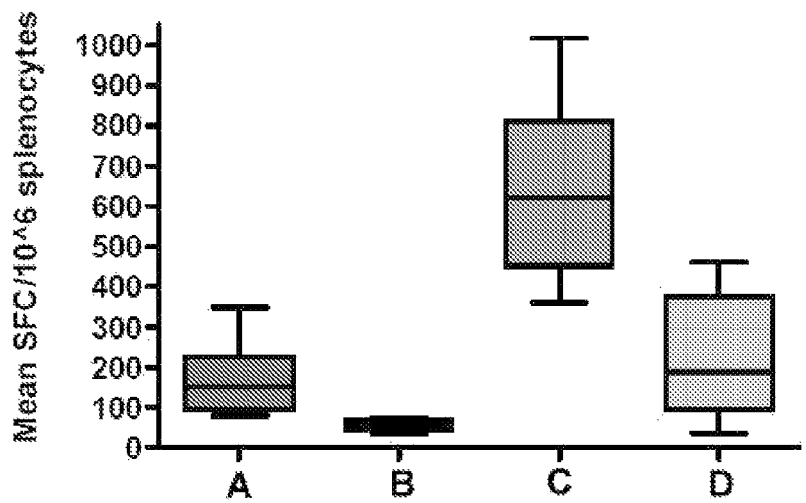
FIG. 10 is a graph illustrating the synergistic enhancement of V3-specific CTL activity following co-administration of HPV/HIV cVLPs with a plasmid DNA construct. In this experiment the cVLPs were formed using full-length HPV16 L1 protein co-expressed and co-assembled with the full-length amino acid sequence of HPV16 L2 protein that was fused in frame at the carboxy-terminus with the amino acid sequence of an HIV Nef-V3-Flag fusion polypeptide. The L1/L2-Nef-V3-Flag cVLPs were then administered either alone or in combination with a plasmid DNA construct that encoded the same HIV Nef-V3-Flag immunogen which was fused at the carboxy-terminus of the coding sequence of rabbit calreticulin (pcDNA3-CRT-Nef-V3-Flag). Female BALB/c mice were immunized by intramuscular injection with pcDNA3-CRT-Nef-V3-Flag plasmid DNA either alone or in combination with the L1/L2-NefV3F cVLPS as indicated. Seven days following the injection, spleen and serum samples were collected for INF-γ ELISpot analysis.

Co-Administration of HPV/HIV cVLP and DNA Synergistically Enhances V3-Specific CTL Activity To evaluate cellular immune responses of animals inoculated simultaneously with both protein and nucleic acid forms of an immunogen, BALB/c mice (N=4 per group) were immunized as follows: A) 50 µg of pcDNA3-CRT-NefV3-Flag DNA plasmid alone; B) 10 µg of 16L1/L2-NefV3-Flag cVLPs alone; or C) with both of these immunogens co-formulated together (i.e., 10 µg of HPV/HIV cVLPs and 50 µg of pcDNA3-CRT-NefV3-Flag plasmid DNA). Primary inoculations were administered on day 0, and booster injections were administered on day 7. On day 14 after primary inoculations splenic V3-specific cellular immune responses were assessed in an IFN-γ ELISpot immunoassay, and results were as follows: modest V3-specific cellular immune responses were obtained in mice that received immunization with 50 µg of DNA or 10 µg of HPV/HIV cVLPs (FIG. 10, compare treatment groups A and B). By contrast, the V3-specific cellular immune response was enhanced synergistically when these immunogens were administered simultaneously. This synergistic response was not observed when the same amount of plasmid DNA was co-administered with non-chimeric L1/L2 VLPs (FIG. 10, compare treatment groups C and D).

Figure 11:
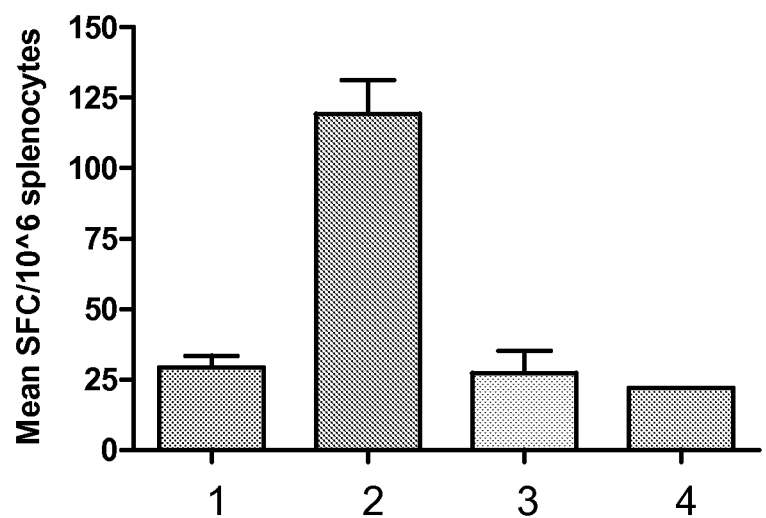
FIG. 11 is a graph showing that co-administration of HPV/HIV cVLPs and plasmid DNA also induces Nef-specific cellular immune responses in addition to the HIV V3-specific responses depicted in FIG. 10. Female C57BL/6 mice were immunized with 10 μg 16L1/L2-Nef-V3-F cVLPs and 50 μg pcDNA3-CRT-Nef-V3-Flag plasmid DNA. Prime inoculation was given on day 0 and boost on day 7. Moderate Nef-specific cellular immune responses were detected as assayed by IFN-γ ELISpot using HIV-1 Nef peptides (HIV-1 Consensus Subtype B Nef (15-mer) Peptides—Complete Set of 49 peptides obtained from NIH AID Research and Reference Reagent Program (ARRRP)). Nef peptides were divided into 4 peptide pools (3 groups of 12 peptides and 1 group of 13 peptides) for the in vitro stimulation of splenocytes in IFN-γ ELISpot assay. The results showed that stronger cellular immune responses were generated against Nef peptide pool #2.

Splenocytes from the same mice were also evaluated by IFN-γ ELISpot assay for Nef-specific responses following stimulation with HIV-1 Nef peptide pools (obtained from NIH ARRRP). The results, shown in FIG. 11, indicated that strong cellular responses were generated against one or more peptides that are contained within ARRRP HIV Nef peptide pool #2.

Figure 12:
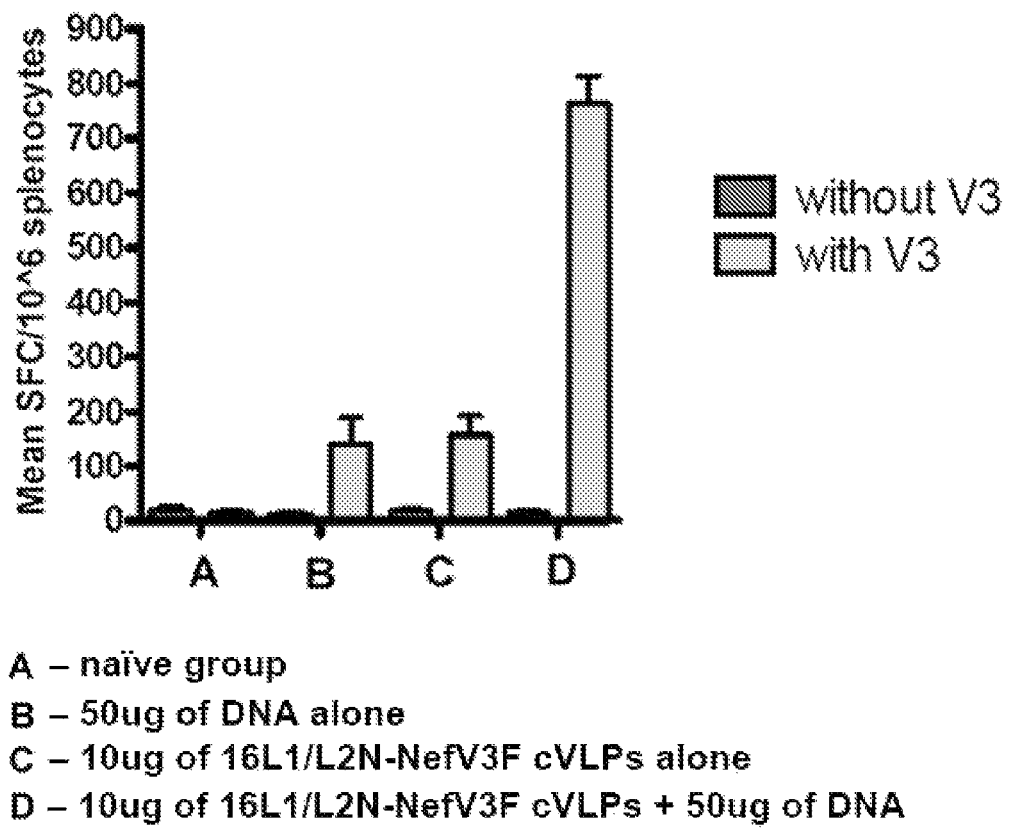
FIG. 12 depicts the synergistic induction of HIV V3-specific cellular immune responses by co-administration of pcDNA3-CRT-NefV3F with cVLPs that were formed using full-length HPV16 L1 protein co-expressed and co-assembled with an alternate L2 fusion protein that consisted of the first 225 amino acid residues of HPV16 L2 ("L2N") fused at the carboxy-terminus with the aforementioned HIV Nef-V3-Flag polypeptide. Thus, in this experiment the cVLPs lacked approximately 50% of L2 carboxy-terminal amino acid residues, which have been shown to mediate enhanced delivery of DNA by facilitating lysosomal egress. Unexpectedly, co-administration of HPV16L1/L2N-NefV3-Flag (which lacked the carboxy-terminal half of L2) with pcDNA3-CRT-Nef-V3-Flag DNA was found to elicit comparable levels of V3-specific cellular immune responses to those obtained when mice were inoculated with plasmid DNA and cVLPs that contained full-length L2-Nef-V3-Flag fusion protein.

It was possible the observed synergistic effect was due to the ability of HPV 16 L2 to facilitate plasmid DNA delivery. Therefore, whether the carboxy-terminal portion of HPV16 L2 was required for the synergistic effect to occur was examined. Mice were immunized with cVLPs that consisted of L1 and carboxy-terminally truncated L2 Nef-V3-Flag fusion protein (i.e., a L2 fusion protein that consisted of L2 amino acids 1-225 ("L2N") fused with HIV Nef-V3-Flag coding sequence) (L1/L2N-Nef-V3-Flag cVLPs). Unexpectedly, a synergistic effect on HIV V3-specific cellular responses was observed when plasmid DNA was co-administered with cVLPs that contained the carboxy-terminally truncated L2N-Nef-V3-Flag protein (FIG. 12, group D). The HIV V3-specific cellular immune response obtained when plasmid DNA was co-administered with cVLPs containing truncated L2N-Nef-V3-Flag fusion protein were significantly stronger than responses obtained in mice that received either nothing (FIG. 12, group A), plasmid DNA alone (FIG. 12, group B), or cVLPs that contained carboxy-terminally truncated L2N-Nef-V3-Flag fusion protein without plasmid DNA (FIG. 12, group C). Thus, the observed synergistic effect on cellular immune responses that was obtained by co-administering HIV Nef-V3-Flag in both protein and nucleic acid forms occurred despite the absence of the carboxy-terminal region of L2 protein, which has been shown to be required for enhancement of DNA delivery.

Figure 13:
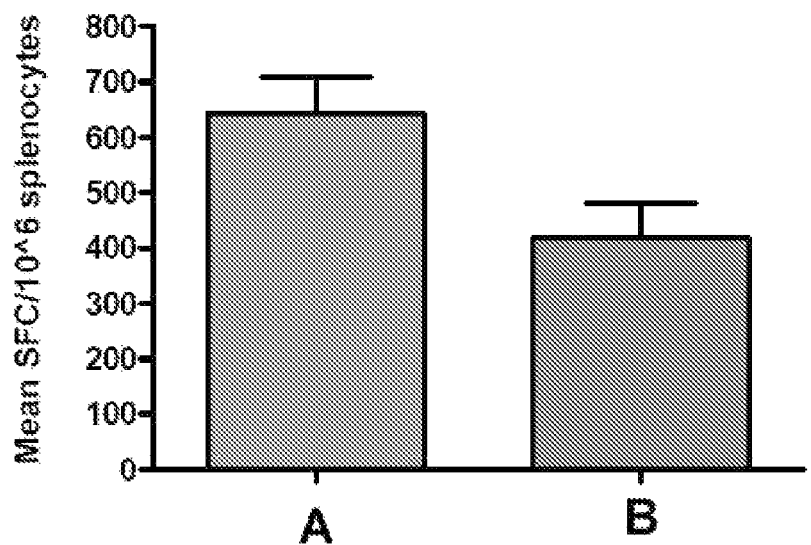
FIG. 13 is a graph demonstrating that co-administration of cVLPs (16L1/L2-NefV3F) and DNA (pcDNA3-CRT-NefV3Flag plasmid) is superior to traditional DNA prime/protein boost strategies. Co-administration of HIV antigen in both cVLPs and DNA as primary and booster injections was compared to the traditional DNA prime and protein boost strategy to determine which strategy was a better method of immunization. One group of mice was immunized with 10 μg of 16L1/L2-NefV3F cVLPs and 50 μg of pcDNA3-CRT-NefV3-Flag DNA, primary on day 0 and booster on day 7. Another group of mice was primed on day 0 with 100 μg of pcDNA3-CRT-NefV3-Flag DNA and boosted on day 7 with 20 μg of 16L1/L2-NefV3F cVLPs. Both groups of mice were given the same total amount of cVLPs and DNA. IFN-γ ELISpot results demonstrated stronger V3-specific cellular immune responses in mice co-administered with cVLPs and DNA. These results indicated that the administration of antigen in both cVLPs and DNA may be superior to the traditional DNA prime and protein boost immunization regimen.

To further examine the temporal aspects of this synergistic phenomenon, mice were administered primary and booster inoculations of 50 µg of CRT-Nef-V3-Flag plasmid DNA co-formulated with 10 µg of L1/L2-Nef-V3-Flag cVLPs (FIG. 13, group A) or 100 µg of CRT-Nef-V3-Flag plasmid DNA as a primary immunization, and then 20 µg of L1/L2-Nef-V3-Flag cVLPs as a booster inoculation (FIG. 13, group B). Thus, both groups of mice received identical amounts of each type of immunogen. Results indicated that simultaneous co-administration of the immunogen in both protein and nucleic acid forms was demonstrably superior to primary inoculation with plasmid DNA followed by boosting with cVLPs (FIG. 13, compare groups A and B).

Figure 14:
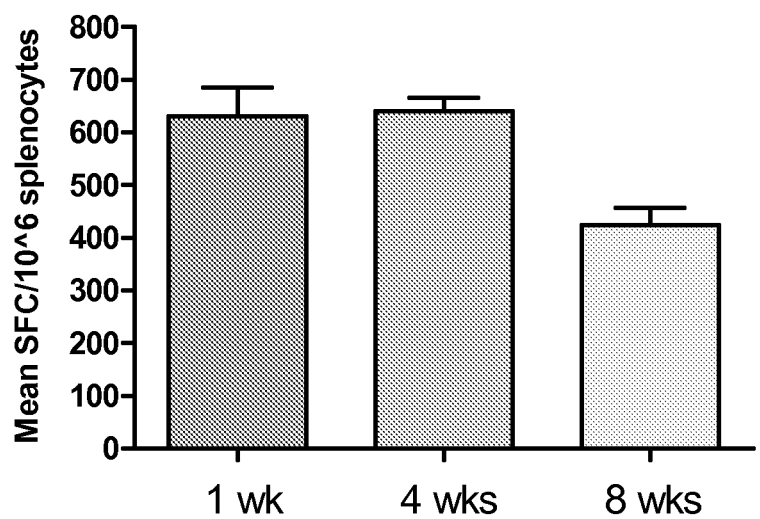
FIG. 14 shows a strong memory response is elicited with cVLP/DNA co-administration. To examine the longevity of cellular immune response induced by co-administration of HPV/HIV cVLPs and DNA, 3 groups of mice were immunized with 10 μg of 16L1/L2-NefV3F cVLPs and 50 μg of pcDNA3-CRT-NefV3-Flag plasmid DNA. Primary and booster injections were given on day 0 and 7, respectively. Spleens were harvested on 7 days, 28 days (4 weeks), and 56 days (8 weeks) after the booster inoculation. IFN-γ ELISpot results demonstrated similar levels of V3-specific cellular immune responses in spleens that were harvested on 7 and 28 days post-immunization. Lower response but nevertheless strong cellular immune responses were detected on 56 days following the booster inoculation.

To determine whether this method of immunization elicits memory responses, three groups of mice were immunized with 10 mg cVLPs co-formulated with 50 mg plasmid DNA, and then sacrificed at three different timepoints following primary and booster inoculations; i.e., at 1 week, 4 weeks, or 8 weeks after booster inoculation. The results, as shown in FIG. 14, indicated that robust memory responses were generated following co-administration of antigen in both protein and nucleic acid forms.

Figure 15:
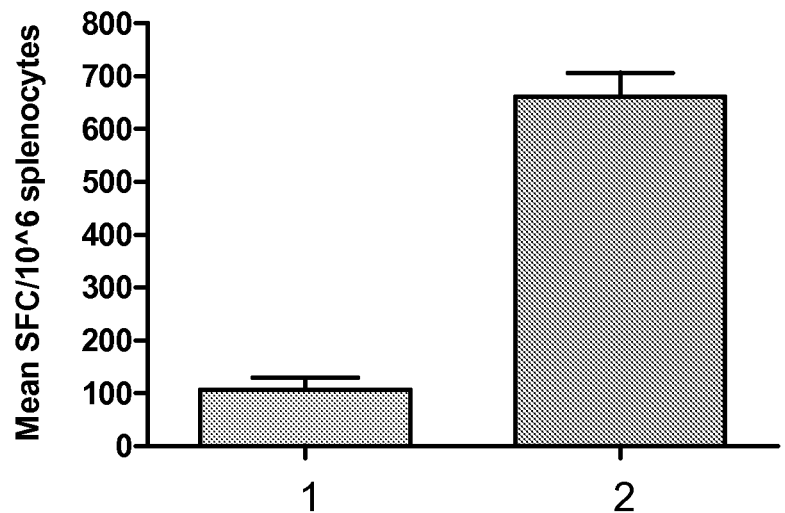
FIG. 15 is a graph comparing intramuscular and intraperitoneal co-administration of cVLP/DNA. Intramuscular administration was found to be superior to intraperitoneal administration for induction of V3-specific cellular immune responses.

Co-administration of cVLPs and DNA administered by alternate (i.e., intraperitoneal versus intramuscular) routes of administration was also examined. Synergistic HIV-specific responses generated via the intramuscular route (FIG. 15, group B) were far superior to those generated via the intraperitoneal route (FIG. 15, group A).

Figure 16:
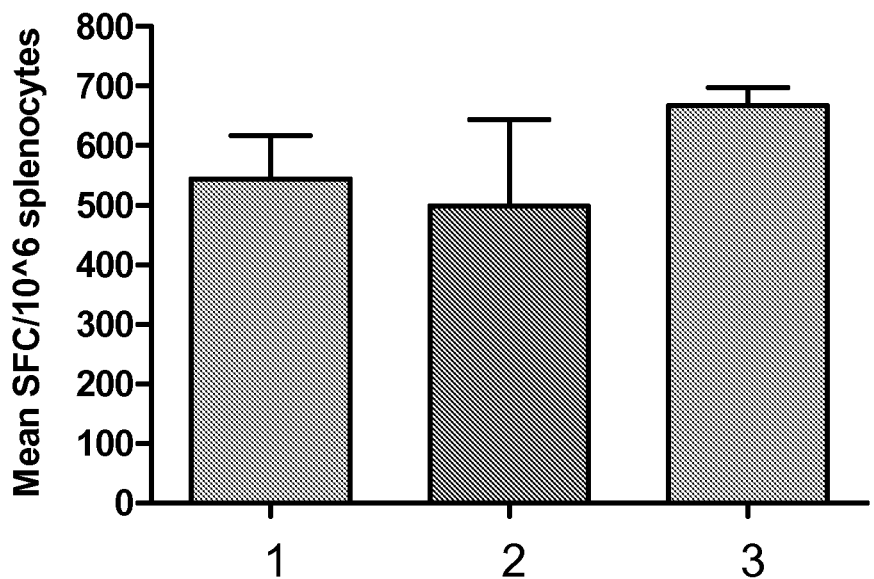
FIG. 16 demonstrates that pre-existing antibodies against 16L1 have no effect on the magnitude of V3-specific cellular immune responses. To circumvent the concern of pre-existing antibody effect on the subsequent immunizations, mice were divided into 3 groups prior to the co-administration of 10 μg of 16L1/L2-NefV3F cVLPs and 50 μg of pcDNA3-CRT-NefV3-Flag plasmid DNA. One group did not receive any prior VLPs while two other groups were injected with either 1 μg of HPV-16L1 VLPs or 1 μg of HPV-11L1 VLPs twice (prime/boost). IFN-γ ELISpot results demonstrated that pre-existing Abs against 16L1 have no effect on the magnitude of V3-specific cellular immune responses.

To determine whether pre-existing HPV genotype-specific capsid antibody responses may interfere with this immunization strategy by "neutralizing" (i.e., binding to and thus preventing uptake of) cVLPs and plasmid DNA, an experiment in which mice were pre-immunized with either nothing, or 1 µg of HPV16-L1 or HPV11-L1 VLPs was performed. It has previously been established that 1 µg of either type of VLP is sufficient to induce strong, high-titer capsid specific neutralizing antibodies against the respective HPV genotype. Following this, all three groups of mice received the standard vaccine regimen (i.e., 10 μg of cVLPs plus 50 μg of plasmid DNA, prime and boost). Results indicated that pre-existing HPV16 L1 capsid-specific antibodies demonstrated no deleterious effect. Indeed, the pre-existing antibodies may have a positive effect on the synergistic induction of HIV V3-specific cellular immune responses compared with responses seen in mice that received either no pre-immunization or pre-immunization with HPV 11 L1 VLPs (FIG. 16).

Figure 17:
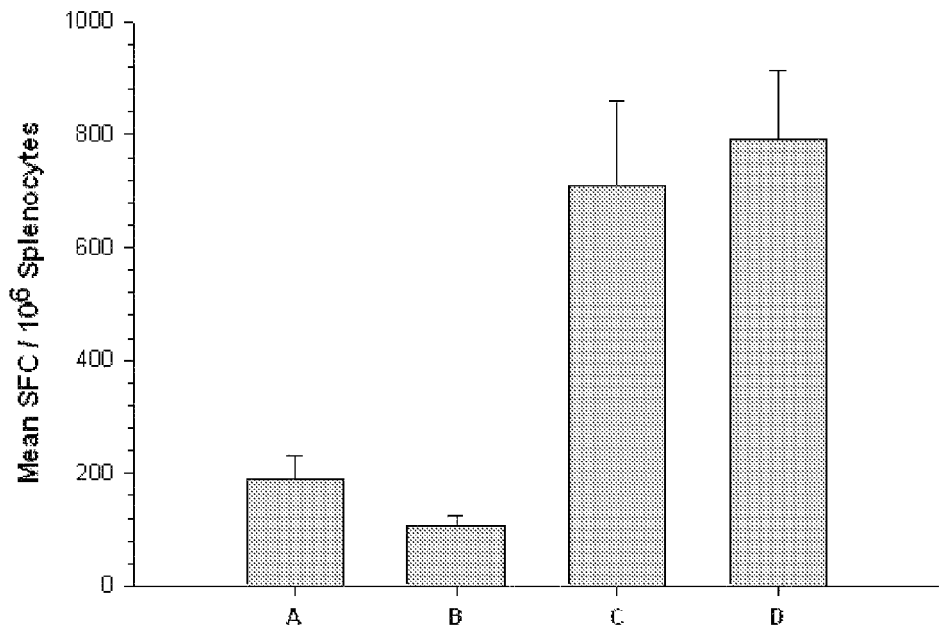
FIG. 17 provides additional evidence to support the conclusion that the synergistic effect obtained by simultaneous co-administration of cVLPs (with or without the L2 carboxy-terminal region) with a plasmid construct designed to encode the same immunogen (in this instance, HIV Nef-V3-Flag) does not depend on the ability of cVLPs to mediate or otherwise enhance plasmid DNA delivery. In this experiment cVLPs (lacking the L2 carboxy-terminal region) and DNA were administered either alone (Groups A and B, respectively) or in combination (Groups C and D) to mice. Inoculations of groups C and D differed in that plasmid DNA and cVLPs were co-administered at essentially the same time, either together in the same anatomic site (left hind leg; Group C) or, alternatively, co-administered at essentially the same time in different anatomic sites (DNA, left hind leg; cVLPs, right hind leg; Group D). Results indicated that simultaneous co-administration of plasmid DNA and cVLPs, either at the same or at disparate anatomic sites, yielded HIV-specific cellular immune responses that essentially were comparable in magnitude.

Lastly, it was confirmed that the synergistic effect observed was not dependent upon VLP-mediated gene delivery, but rather on the coincident administration of the immunogen in both protein and nucleic acid forms. In this experiment mice received cVLPs (lacking the L2 carboxy-terminal region) and plasmid DNA at the same time, but in one group of mice immunogens were co-administered in the same anatomic site (i.e., hind leg) and in the other group of mice the immunogens were co-administered at the same time but in different anatomic sites (i.e., alternate hind legs). The results, as shown in FIG. 17, indicated that simultaneous co-administration of plasmid DNA and cVLPs either at the same or disparate anatomic sites yielded HIV-specific cellular immune responses that essentially were comparable in magnitude.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

SEQUENCE LISTING

<160> NUMBER OF SEQ ID NOS: 13

<210> SEQ ID NO 1
<211> LENGTH: 15
<212> TYPE: PRT
<213> ORGANISM: Artificial
<220> FEATURE:
<223> OTHER INFORMATION: HIV NefV3 Epitope

<400> SEQUENCE: 1

Arg Ile Gln Arg Gly Pro Gly Arg Ala Phe Val Thr Ile Gly Lys
1               5                   10                  15

<210> SEQ ID NO 2
<211> LENGTH: 435
<212> TYPE: PRT
<213> ORGANISM: Artificial
<220> FEATURE:
<223> OTHER INFORMATION: L2N-Nef-V3

<400> SEQUENCE: 2

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
                20                  25                  30

Ile Pro Lys Val Glu Gly Lys Thr Ile Ala Glu Gln Ile Leu Gln Tyr
            35                  40                  45

Gly Ser Met Gly Val Phe Phe Gly Gly Leu Gly Ile Gly Thr Gly Ser
        50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
            195                 200                 205

Thr Val Thr Ser Ser Thr Pro Ile Pro Gly Ser Arg Pro Val Ala Arg
        210                 215                 220

Leu Met Arg Arg Ala Glu Pro Ala Ala Glu Gly Val Gly Ala Val Ser
225                 230                 235                 240

Arg Asp Leu Glu Lys His Gly Ala Ile Thr Ser Ser Asn Thr Ala Ala
            245                 250                 255

Thr Asn Ala Ala Cys Ala Trp Leu Glu Ala Gln Glu Glu Glu Glu Val
                260                 265                 270

Gly Phe Pro Val Arg Pro Gln Val Pro Leu Arg Pro Met Thr Tyr Lys
            275                 280                 285

Ala Ala Val Asp Leu Ser His Phe Leu Lys Glu Lys Gly Gly Leu Glu
        290                 295                 300

Gly Leu Ile Tyr Ser Gln Lys Arg Gln Asp Ile Leu Asp Leu Trp Val
305                 310                 315                 320

Tyr His Thr Gln Gly Tyr Phe Pro Asp Trp Gln Asn Tyr Thr Pro Gly
                325                 330                 335

Pro Gly Ile Arg Tyr Pro Leu Thr Phe Gly Trp Cys Phe Lys Leu Val
            340                 345                 350

Pro Val Glu Pro Glu Lys Val Glu Glu Ala Asn Glu Gly Glu Asn Asn
        355                 360                 365

Cys Leu Leu His Pro Met Ser Gln His Gly Met Asp Asp Pro Glu Lys
    370                 375                 380

Glu Val Leu Val Trp Lys Phe Asp Ser Lys Leu Ala Phe His His Met
385                 390                 395                 400

Ala Arg Glu Leu His Pro Glu Tyr Tyr Lys Asp Cys Arg Ile Gln Arg
                405                 410                 415

Gly Pro Gly Arg Ala Phe Val Thr Ile Gly Lys Asp Tyr Lys Asp Asp
            420                 425                 430

Asp Asp Lys
        435

<210> SEQ ID NO 3
<211> LENGTH: 1308
<212> TYPE: DNA
<213> ORGANISM: Artificial
<220> FEATURE:
<223> OTHER INFORMATION: L2N-Nef-V3

<400> SEQUENCE: 3
atgcgacaca aacgttctgc aaaacgcaca aacgtgcat cggctaccca actttataaa      60
acatgcaaac aggcaggtac atgtccacct gacattatac taaggttgaa aggcaaaact    120
attgctgaac aaatattaca atatggaagt atgggtgtat tttttggtgg gttaggaatt    180
ggaacagggt cgggtacagg cggacgcact gggtatattc cattgggaac aaggcctccc    240
acagctacag atacacttgc tcctgtaaga ccccctttaa cagtagatcc tgtgggccct    300
tctgatcctt ctatagtttc tttagtggaa gaaactagtt ttattgatgc tggtgcacca    360
acatctgtac cttccattcc cccagatgta tcaggattta gtattactac ttcaactgat    420
accacacctg ctatattaga tattaataat actgttacta ctgttactac acataataat    480
cccactttca ctgacccatc tgtattgcag cctccaacac ctgcagaaac tggagggcat    540
tttacacttt catcatccac tattagtaca cataattatg aagaaattcc tatggataca    600

-continued

```
tttattgtta gcacaaaccc taacacagta actagtagca cacccatacc agggtctcgc      660
ccagtggcac gcctaatgag gcgagctgag ccagcagcag agggagtggg agcagtatct      720
cgagacctgg aaaaacatgg agcaattaca gtagcaata cagcagctac caatgctgct      780
tgtgcctggc tagaagcaca agaggaggaa gaagtgggtt ttccagtcag acctcaggta      840 ccctttaagac caatgactta caaggcagca gtagatctta gccactttttt aaagaaaag    900 gggggactgg aagggttaat ttactcccaa aaaagacaag atatccttga tctgtgggtc      960
taccacacac aaggctactt ccctgattgg cagaactaca caccagggcc aggaatcaga     1020
tatccactga cctttgggtg gtgcttcaaa ctagtaccag ttgagccaga aaggtagaa      1080 gaggccaatg aaggagagaa caactgcttg ctacaccta tgagccagca tgggatggat     1140
gacccagaga aagaagtatt agtgtggaag tttgacagca aactagcatt tcatcacatg     1200
gcccgagagc tgcatccgga gtactacaaa gactgccgaa tccaacgcgg accaggtcga     1260
gcatttgtaa caattggaaa agactacaag gacgacgatg acaagtag                 1308
```

<210> SEQ ID NO 4
<211> LENGTH: 683
<212> TYPE: PRT
<213> ORGANISM: Artificial
<220> FEATURE:
<223> OTHER INFORMATION: L2(full)-Nef-V3

<400> SEQUENCE: 4

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240
```

```
Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
                340                 345                 350

Ser His Ala Ala Ser Pro Thr Ser Ile Asn Asn Gly Leu Tyr Asp Ile
            355                 360                 365

Tyr Ala Asp Asp Phe Ile Thr Asp Thr Ser Thr Pro Val Pro Ser
    370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Lys Arg Leu Pro Tyr
    450                 455                 460

Phe Phe Ser Asp Val Ser Leu Ala Ala Met Arg Arg Ala Glu Pro Ala
465                 470                 475                 480

Ala Glu Gly Val Gly Ala Val Ser Arg Asp Leu Glu Lys His Gly Ala
                485                 490                 495

Ile Thr Ser Ser Asn Thr Ala Thr Asn Ala Ala Cys Ala Trp Leu
            500                 505                 510

Glu Ala Gln Glu Glu Glu Val Gly Phe Pro Val Arg Pro Gln Val
        515                 520                 525

Pro Leu Arg Pro Met Thr Tyr Lys Ala Ala Val Asp Leu Ser His Phe
    530                 535                 540

Leu Lys Glu Lys Gly Gly Leu Glu Gly Leu Ile Tyr Ser Gln Lys Arg
545                 550                 555                 560

Gln Asp Ile Leu Asp Leu Trp Val Tyr His Thr Gln Gly Tyr Phe Pro
                565                 570                 575

Asp Trp Gln Asn Tyr Thr Pro Gly Pro Gly Ile Arg Tyr Pro Leu Thr
            580                 585                 590

Phe Gly Trp Cys Phe Lys Leu Val Pro Val Glu Pro Glu Lys Val Glu
        595                 600                 605

Glu Ala Asn Glu Gly Glu Asn Asn Cys Leu Leu His Pro Met Ser Gln
    610                 615                 620

His Gly Met Asp Asp Pro Glu Lys Glu Val Leu Val Trp Lys Phe Asp
625                 630                 635                 640

Ser Lys Leu Ala Phe His His Met Ala Arg Glu Leu His Pro Glu Tyr
                645                 650                 655

Tyr Lys Asp Cys Arg Ile Gln Arg Gly Pro Gly Arg Ala Phe Val Thr
```

660              665              670
Ile Gly Lys Asp Tyr Lys Asp Asp Asp Asp Lys
        675              680

<210> SEQ ID NO 5
<211> LENGTH: 2052
<212> TYPE: DNA
<213> ORGANISM: Artificial
<220> FEATURE:
<223> OTHER INFORMATION: L2(full)-Nef-V3

<400> SEQUENCE: 5

```
atgcgacaca acgttctgc aaaacgcaca aacgtgcat cggctaccca actttataaa      60
acatgcaaac aggcaggtac atgtccacct gacattatac ctaaggttga aggcaaaact     120
attgctgaac aaatattaca atatggaagt atgggtgtat ttttggtgg gttaggaatt     180
ggaacagggt cgggtacagg cggacgcact gggtatattc cattgggaac aaggcctccc     240
acagctacag atacacttgc tcctgtaaga ccccctttaa cagtagatcc tgtgggccct     300
tctgatcctt ctatagtttc tttagtggaa gaaactagtt ttattgatgc tggtgcacca     360
acatctgtac cttccattcc cccagatgta tcaggattta gtattactac ttcaactgat     420
accacacctg ctatattaga tattaataat actgttacta ctgttactac acataataat     480
cccactttca ctgacccatc tgtattgcag cctccaacac tgcagaaaac tggagggcat     540
tttacacttt catcatccac tattagtaca cataattatg aagaaattcc tatggataca     600
tttattgtta gcacaaaccc taacacagta actagtagca cacccatacc agggtctcgc     660
ccagtggcac gcctaggatt atatagtcgc acaacacaac aggttaaagt tgtagaccct     720
gcttttgtaa ccactcccac taaacttatt acatatgata tcctgcata tgaaggtata     780
gatgtggata atacattata ttttctagt aatgataata gtattaatat agctccagat     840
cctgactttt tggatatagt tgctttacat aggccagcat taacctctag gcgtactggc     900
attaggtaca gtagaattgg taataaacaa acactacgta ctcgtagtgg aaaatctata     960
ggtgctaagg tacattatta ttatgattta agtactattg atcctgcaga gaaatagaa    1020
ttacaaacta taacaccttc tacatatact accacttcac atgcagcctc acctacttct    1080
attaataatg gattatatga tatttatgca gatgactta ttacagatac ttctacaacc    1140
ccggtaccat ctgtaccctc tacatcttta tcaggttata ttcctgcaaa tacaacaatt    1200
cctttttggtg gtgcatacaa tattccttta gtatcaggtc ctgatatacc cattaatata    1260
actgaccaag ctccttcatt aattcctata gttccagggt ctccacaata tacaattatt    1320
gctgatgcag gtgactttta tttacatcct agttattaca tgttacgaaa acgacgtaaa    1380
cgtttaccat attttttttc agatgtctct ttggctgcca tgaggcgagc tgagccagca    1440
gcagagggag tgggagcagt atctcgagac ctggaaaaac atggagcaat tacaagtagc    1500
aatacagcag ctaccaatgc tgcttgtgcc tggctagaag cacaagagga ggaagaagtg    1560
ggttttccag tcagacctca ggtaccttta agaccaatga cttacaaggc agcagtagat    1620
cttagccact tttaaaaga aaaggggggga ctggaagggt taatttactc ccaaaaaaga    1680
caagatatcc ttgatctgtg gtctaccac acacaaggct acttccctga ttggcagaac    1740
tacacaccag ggccaggaat cagatatcca ctgacctttg gtggtgcttt caaactagta    1800
ccagttgagc cagagaaggt agaagaggcc aatgaaggag agaacaactg cttgctacac    1860
cctatgagcc agcatgggat ggatgaccca gagaaagaag tattagtgtg gaagtttgac    1920
```

```
agcaaactag catttcatca catggcccga gagctgcatc cggagtacta caaagactgc    1980
cgaatccaac gcggaccagg tcgagcattt gtaacaattg aaaagactca caaggacgac    2040
gatgacaagt ag                                                        2052
```

```
<210> SEQ ID NO 6
<211> LENGTH: 628
<212> TYPE: PRT
<213> ORGANISM: Artificial
<220> FEATURE:
<223> OTHER INFORMATION: CRT-Nef-V3-Flag

<400> SEQUENCE: 6

Met Leu Leu Pro Val Pro Leu Leu Gly Leu Leu Gly Leu Ala Ala
1               5                   10                  15

Ala Glu Pro Val Val Tyr Phe Lys Glu Gln Phe Leu Asp Gly Asp
                20                  25                  30

Gly Trp Thr Glu Arg Trp Ile Glu Ser Lys His Lys Ser Asp Phe Gly Lys
                35                  40                  45

Phe Val Leu Ser Ser Gly Lys Phe Tyr Gly Asp Gln Glu Lys Asp Lys
    50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Phe Thr
                85                  90                  95

Val Lys His Glu Gln Asn Ile Asp Cys Gly Gly Gly Tyr Val Lys Leu
                100                 105                 110

Phe Pro Ala Gly Leu Asp Gln Lys Asp Met His Gly Asp Ser Glu Tyr
            115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Ala Asn
    290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335
```

```
Ala Tyr Ala Glu Glu Phe Gly Asn Glu Thr Trp Gly Val Thr Lys Thr
                340                 345                 350

Ala Glu Lys Gln Met Lys Asp Lys Gln Asp Glu Glu Gln Arg Leu Lys
            355                 360                 365

Glu Glu Glu Glu Glu Lys Lys Arg Lys Glu Glu Glu Glu Ala Glu Glu
        370                 375                 380

Asp Glu Glu Asp Lys Asp Asp Lys Glu Asp Glu Asp Glu Asp Glu Glu
385                 390                 395                 400

Asp Lys Asp Glu Glu Glu Glu Ala Ala Ala Gly Gln Ala Lys Asp
                405                 410                 415

Glu Leu Met Arg Arg Ala Glu Pro Ala Ala Glu Gly Val Gly Ala Val
            420                 425                 430

Ser Arg Asp Leu Glu Lys His Gly Ala Ile Thr Ser Ser Asn Thr Ala
        435                 440                 445

Ala Thr Asn Ala Ala Cys Ala Trp Leu Glu Ala Gln Glu Glu Glu Glu
    450                 455                 460

Val Gly Phe Pro Val Arg Pro Gln Val Pro Leu Arg Pro Met Thr Tyr
465                 470                 475                 480

Lys Ala Ala Val Asp Leu Ser His Phe Leu Lys Glu Lys Gly Gly Leu
                485                 490                 495

Glu Gly Leu Ile Tyr Ser Gln Lys Arg Gln Asp Ile Leu Asp Leu Trp
            500                 505                 510

Val Tyr His Thr Gln Gly Tyr Phe Pro Asp Trp Gln Asn Tyr Thr Pro
        515                 520                 525

Gly Pro Gly Ile Arg Tyr Pro Leu Thr Phe Gly Trp Cys Phe Lys Leu
    530                 535                 540

Val Pro Val Glu Pro Glu Lys Val Glu Glu Ala Asn Glu Gly Glu Asn
545                 550                 555                 560

Asn Cys Leu Leu His Pro Met Ser Gln His Gly Met Asp Asp Pro Glu
                565                 570                 575

Lys Glu Val Leu Val Trp Lys Phe Asp Ser Lys Leu Ala Phe His His
            580                 585                 590

Met Ala Arg Glu Leu His Pro Glu Tyr Tyr Lys Asp Cys Arg Ile Gln
        595                 600                 605

Arg Gly Pro Gly Arg Ala Phe Val Thr Ile Gly Lys Asp Tyr Lys Asp
    610                 615                 620

Asp Asp Asp Lys
625

<210> SEQ ID NO 7
<211> LENGTH: 1887
<212> TYPE: DNA
<213> ORGANISM: Artificial
<220> FEATURE:
<223> OTHER INFORMATION: CRT-Nef-V3-Flag

<400> SEQUENCE: 7
atgctgctcc ctgtgccgct gctgctcggc ctgctcggcc tggccgccgc cgagcccgtc      60
gtctacttca aggagcagtt tctggacgga gatgggtgga ccgagcgctg gatcgaatcc     120
aaacacaagt ccgattttgg caaattcgtc ctcagttcgg caagttcta cggcgatcag      180 gagaaagata aagggctgca gaccagccag gacgcccgct ctacgccct gtcggcccga     240 ttcgagccgt tcagcaacaa gggccagcca ctggtggtgc agttcaccgt gaaacacgag     300
cagaacattg actgcggggg cggctacgtg aagctgtttc cggccggcct ggaccagaag     360
```

```
gacatgcacg gggactctga gtacaacatc atgtttggtc ctgacatctg tggccccggc    420
accaagaagg ttcacgtcat cttcaactac aagggcaaga acgtgctgat caacaaggac    480
atccgttgca aggacgacga gttcacacac ctgtacacgc tgatcgtgcg gccggacaac    540
acgtatgagg tgaagattga caacagccag gtggagtcgg gctccctgga ggatgactgg    600
gacttcctac cccccaagaa gataaaggac ccagatgcct cgaagcctga agactgggac    660
gagcgggcca agatcgacga ccccacggac tccaagcccg aggactggga caagcccgag    720
cacatccccg acccggacgc gaagaagccc gaagactggg acgaagaaat ggacggagag    780
tgggagccgc cggtgattca gaaccccgag tacaagggtg agtggaagcc gcggcagatc    840
gacaaccccg attacaaagg cacctggatc caccccgaaa tcgacaaccc cgagtactcg    900
cccgacgcta acatctatgc ctacgacagc tttgccgtgc tgggcttgga cctctggcag    960
gtcaagtcgg gcaccatctt cgacaacttc ctcatcacca acgatgaggc gtacgcagag   1020
gagtttggca cgagacgtg gggcgtcacc aagacggccg agaagcagat gaaagacaag   1080
caggacgagg agcagcggct gaaggaggag gaggaggaga agaagcggaa ggaggaggag   1140
gaggccgagg aggacgagga ggacaaggac gacaaggagg acgaggatga ggacgaggag   1200
gacaaggacg aggaggagga ggaggcggcc gccggccagg ccaaggacga gctgatgagg   1260
cgagctgagc cagcagcaga gggagtggga gcagtatctc gagacctgga aaaacatgga   1320
gcaattacaa gtagcaatac agcagctacc aatgctgctt gtgcctggct agaagcacaa   1380
gaggaggaag aagtgggttt ccagtcaga cctcaggtac ctttaagacc aatgacttac   1440
aaggcagcag tagatcttag ccactttta aaagaaaagg ggggactgga agggttaatt   1500
tactcccaaa aaagacaaga tatccttgat ctgtgggtct accacacaca aggctacttc   1560
cctgattggc agaactacac accagggcca ggaatcagat atccactgac ctttgggtgg   1620
tgcttcaaac tagtaccagt tgagccagag aaggtagaag aggccaatga aggagagaac   1680
aactgcttgc tacaccctat gagccagcat gggatggatg acccagagaa agaagtatta   1740
gtgtggaagt ttgacagcaa actagcattt catcacatgg cccgagagct gcatccggag   1800
tactacaaag actgccgaat ccaacgcgga ccaggtcgag catttgtaac aattggaaaa   1860
gactacaagg acgacgatga caagtag                                       1887
```

<210> SEQ ID NO 8
<211> LENGTH: 383
<212> TYPE: PRT
<213> ORGANISM: artificial
<220> FEATURE:
<223> OTHER INFORMATION: L2N-E6

<400> SEQUENCE: 8

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
            85                  90                  95
```

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
            115                 120                 125

Asp Val Ser Gly Phe Ser Ile Thr Thr Ser Thr Asp Thr Thr Pro Ala
        130                 135                 140

Ile Leu Asp Ile Asn Asn Thr Val Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Met His Gln Lys Arg Thr Ala Met Phe Gln Asp Pro Gln Glu Arg
225                 230                 235                 240

Pro Arg Lys Leu Pro His Leu Cys Thr Glu Leu Gln Thr Thr Ile His
                245                 250                 255

Asp Ile Ile Leu Glu Cys Val Tyr Cys Lys Gln Gln Leu Leu Arg Arg
            260                 265                 270

Glu Val Tyr Asp Phe Ala Phe Arg Asp Leu Cys Ile Val Tyr Arg Asp
        275                 280                 285

Gly Asn Pro Tyr Ala Val Cys Asp Lys Cys Leu Lys Phe Tyr Ser Lys
    290                 295                 300

Ile Ser Glu Tyr Arg Tyr Tyr Cys Tyr Ser Val Tyr Gly Thr Thr Leu
305                 310                 315                 320

Glu Gln Gln Tyr Asn Lys Pro Leu Cys Asp Leu Leu Ile Arg Cys Ile
                325                 330                 335

Asn Cys Gln Lys Pro Leu Cys Pro Glu Glu Lys Gln Arg His Leu Asp
            340                 345                 350

Lys Lys Gln Arg Phe His Asn Ile Arg Gly Arg Trp Thr Gly Arg Cys
        355                 360                 365

Met Ser Cys Cys Arg Ser Ser Arg Thr Arg Arg Glu Thr Gln Leu
    370                 375                 380

<210> SEQ ID NO 9
<211> LENGTH: 1152
<212> TYPE: DNA
<213> ORGANISM: artificial
<220> FEATURE:
<223> OTHER INFORMATION: L2N-E6

<400> SEQUENCE: 9
atgcgacaca acgttctgc aaaacgcaca aaacgtgcat cggctaccca actttataaa      60
acatgcaaac aggcaggtac atgtccacct gacattatac ctaaggttga aggcaaaact    120
attgctgaac aaatattaca atatggaagt atgggtgtat tttttggtgg gttaggaatt    180
ggaacagggt cgggtacagg cggacgcact gggtatattc cattgggaac aaggcctccc    240
acagctacag atacacttgc tcctgtaaga ccccctttaa cagtagatcc tgtgggccct    300
tctgatcctt ctatagtttc tttagtggaa gaaactagtt ttattgatgc tggtgcacca    360
acatctgtac cttccattcc cccagatgta tcaggattta gtattactac ttcaactgat    420

```
accacacctg ctatattaga tattaataat actgttacta ctgttactac acataataat    480
cccactttca ctgacccatc tgtattgcag cctccaacac ctgcagaaac tggagggcat    540
tttacacttt catcatccac tattagtaca cataattatg aagaaattcc tatggataca    600
tttattgtta gcacaaaccc taacacagta actagtagca cacccatacc agggtctcgc    660
ccagtggcac gcctaatgca ccaaaagaga actgcaatgt tcaggaccc acaggagcga    720
cccagaaagt taccacagtt atgcacagag ctgcaaacaa ctatacatga tataatatta    780
gaatgtgtgt actgcaagca acagttactg cgacgtgagg tatatgactt tgcttttcgg    840
gatttatgca tagtatatag agatgggaat ccatatgctg tatgtgataa atgtttaaag    900
ttttattcta aaattagtga gtatagacat tattgttata gtttgtatgg aacaacatta    960
gaacagcaat acaacaaacc gttgtgtgat ttgttaatta ggtgtattaa ctgtcaaaag   1020
ccactgtgtc ctgaagaaaa gcaaagacat ctggacaaaa agcaaagatt ccataatata   1080
aggggtcggt ggaccggtcg atgtatgtct tgttgcagat catcaagaac acgtagagaa   1140
acccagctgt aa                                                      1152
```

<210> SEQ ID NO 10
<211> LENGTH: 631
<212> TYPE: PRT
<213> ORGANISM: artificial
<220> FEATURE:
<223> OTHER INFORMATION: L2(full)-E6

<400> SEQUENCE: 10

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
```

```
              225                 230                 235                 240
Ala Phe Val Thr Thr Pro Thr Lys Leu Ile Thr Tyr Asp Asn Pro Ala
                245                 250                 255
Tyr Glu Gly Ile Asp Val Asp Asn Thr Leu Tyr Phe Ser Ser Asn Asp
                260                 265                 270
Asn Ser Ile Asn Ile Ala Pro Asp Pro Asp Phe Leu Asp Ile Val Ala
            275                 280                 285
Leu His Arg Pro Ala Leu Thr Ser Arg Arg Thr Gly Ile Arg Tyr Ser
        290                 295                 300
Arg Ile Gly Asn Lys Gln Thr Leu Arg Thr Arg Ser Gly Lys Ser Ile
305                 310                 315                 320
Gly Ala Lys Val His Tyr Tyr Asp Leu Ser Thr Ile Asp Pro Ala
                325                 330                 335
Glu Glu Ile Glu Leu Gln Thr Ile Thr Pro Ser Thr Tyr Thr Thr Thr
                340                 345                 350
Ser His Ala Ala Ser Pro Thr Ser Ile Asn Asn Gly Leu Tyr Asp Ile
            355                 360                 365
Tyr Ala Asp Asp Phe Ile Thr Asp Thr Ser Thr Thr Pro Val Pro Ser
        370                 375                 380
Val Pro Ser Thr Ser Leu Ser Gly Tyr Ile Pro Ala Asn Thr Thr Ile
385                 390                 395                 400
Pro Phe Gly Gly Ala Tyr Asn Ile Pro Leu Val Ser Gly Pro Asp Ile
                405                 410                 415
Pro Ile Asn Ile Thr Asp Gln Ala Pro Ser Leu Ile Pro Ile Val Pro
                420                 425                 430
Gly Ser Pro Gln Tyr Thr Ile Ile Ala Asp Ala Gly Asp Phe Tyr Leu
            435                 440                 445
His Pro Ser Tyr Tyr Met Leu Arg Lys Arg Lys Arg Leu Pro Tyr
        450                 455                 460
Phe Phe Ser Asp Val Ser Leu Ala Ala Met His Gln Lys Arg Thr Ala
465                 470                 475                 480
Met Phe Gln Asp Pro Gln Glu Arg Pro Arg Lys Leu Pro His Leu Cys
                485                 490                 495
Thr Glu Leu Gln Thr Thr Ile His Asp Ile Ile Leu Glu Cys Val Tyr
                500                 505                 510
Cys Lys Gln Gln Leu Leu Arg Arg Glu Val Tyr Asp Phe Ala Phe Arg
            515                 520                 525
Asp Leu Cys Ile Val Tyr Arg Asp Gly Asn Pro Tyr Ala Val Cys Asp
        530                 535                 540
Lys Cys Leu Lys Phe Tyr Ser Lys Ile Ser Glu Tyr Arg Tyr Tyr Cys
545                 550                 555                 560
Tyr Ser Val Tyr Gly Thr Thr Leu Glu Gln Tyr Asn Lys Pro Leu
                565                 570                 575
Cys Asp Leu Leu Ile Arg Cys Ile Asn Cys Gln Lys Pro Leu Cys Pro
            580                 585                 590
Glu Glu Lys Gln Arg His Leu Asp Lys Lys Gln Arg Phe His Asn Ile
        595                 600                 605
Arg Gly Arg Trp Thr Gly Arg Cys Met Ser Cys Arg Ser Ser Arg
        610                 615                 620
Thr Arg Arg Glu Thr Gln Leu
625                 630

<210> SEQ ID NO 11
```

<211> LENGTH: 1896
<212> TYPE: DNA
<213> ORGANISM: artificial
<220> FEATURE:
<223> OTHER INFORMATION: L2(full)-E6

<400> SEQUENCE: 11

```
atgcgacaca acgttctgc aaaacgcaca aaacgtgcat cggctaccca actttataaa      60
acatgcaaac aggcaggtac atgtccacct gacattatac ctaaggttga aggcaaaact     120
attgctgaac aaatattaca atatggaagt atgggtgtat tttttggtgg gttaggaatt     180
ggaacagggt cgggtacagg cggacgcact gggtatattc cattgggaac aaggcctccc     240
acagctacag atacacttgc tcctgtaaga cccccttta cagtagatcc tgtgggccct     300
tctgatcctt ctatagtttc tttagtggaa gaaactagtt ttattgatgc tggtgcacca     360
acatctgtac cttccattcc cccagatgta tcaggattta gtattactac ttcaactgat     420
accacacctg ctatattaga tattaataat actgttacta ctgttactac acataataat     480
cccactttca ctgacccatc tgtattgcag cctccaacac ctgcagaaac tggagggcat     540
tttacacttt catcatccac tattagtaca cataattatg aagaaattcc tatggataca     600
tttattgtta gcacaaaccc taacacagta actagtagca cccataccc agggtctcgc     660
ccagtggcac gcctaggatt atatagtcgc acaacacaac aggttaaagt tgtagaccct     720
gcttttgtaa ccactcccac taaacttatt acatatgata atcctgcata tgaaggtata     780
gatgtggata tacattata ttttctagt aatgataata gtattaatat agctccagat     840
cctgactttt tggatatagt tgctttacat aggccagcat taacctctag cgtactggc      900
attaggtaca gtagaattgg taataaacaa acactacgta ctcgtagtgg aaaatctata     960
ggtgctaagg tacattatta ttatgattta agtactattg atcctgcaga gaaaatagaa    1020
ttacaaacta taacaccttc tacatatact accacttcac atgcagcctc acctacttct    1080
attaataatg gattatatga tatttatgca gatgactttt tacagatac ttctacaacc    1140
ccggtaccat ctgtaccctc tacatcttta tcaggttata ttcctgcaaa tacaacaatt    1200
ccttttggtg gtgcatacaa tattccttta gtatcaggtc ctgatatacc cattaatata    1260
actgaccaag ctccttcatt aattcctata gttccagggt ctccacaata caattatt     1320
gctgatgcag gtgacttta tttacatcct agttattaca tgttacgaaa acgacgtaaa    1380
cgtttaccat atttttttc agatgtctct ttggctgcca tgcaccaaaa gagaactgca    1440
atgtttcagg acccacagga gcgacccaga aagttaccac agttatgcac agagctgcaa    1500
acaactatac atgatataat attagaatgt gtgtactgca agcaacagtt actgcgacgt    1560
gaggtatatg actttgcttt tcgggattta tgcatagtat atagagatgg gaatccatat    1620
gctgtatgtg ataaatgttt aaagttttat tctaaaatta gtgagtatag acattattgt    1680
tatagtttgt atggaacaac attagaacag caatacaaca accgttgtg tgatttgtta    1740
attaggtgta ttaactgtca aaagccactg tgtcctgaag aaaagcaaag acatctggac    1800
aaaaagcaaa gattccataa tataagggt cggtggaccg tcgatgtat gtcttgttgc    1860
agatcatcaa gaacacgtag agaaacccag ctgtaa                             1896
```

<210> SEQ ID NO 12
<211> LENGTH: 576
<212> TYPE: PRT
<213> ORGANISM: artificial
<220> FEATURE:
<223> OTHER INFORMATION: CRF-E6

<400> SEQUENCE: 12

```
Met Leu Leu Pro Val Pro Leu Leu Gly Leu Leu Gly Leu Ala Ala
1               5                   10                  15

Ala Glu Pro Val Val Tyr Phe Lys Glu Gln Phe Leu Asp Gly Asp Gly
            20                  25                  30

Trp Thr Glu Arg Trp Ile Glu Ser Lys His Lys Ser Asp Phe Gly Lys
            35                  40                  45

Phe Val Leu Ser Ser Gly Lys Phe Tyr Gly Asp Gln Glu Lys Asp Lys
        50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Phe Thr
                85                  90                  95

Val Lys His Glu Gln Asn Ile Asp Cys Gly Gly Gly Tyr Val Lys Leu
            100                 105                 110

Phe Pro Ala Gly Leu Asp Gln Lys Asp Met His Gly Asp Ser Glu Tyr
        115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Ala Asn
290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Thr
            340                 345                 350

Ala Glu Lys Gln Met Lys Asp Lys Gln Asp Glu Glu Gln Arg Leu Lys
        355                 360                 365

Glu Glu Glu Glu Glu Lys Lys Arg Lys Glu Glu Glu Glu Ala Glu Glu
        370                 375                 380

Asp Glu Glu Asp Lys Asp Asp Lys Glu Asp Glu Asp Glu Asp Glu Glu
385                 390                 395                 400

Asp Lys Asp Glu Glu Glu Glu Glu Ala Ala Ala Gly Gln Ala Lys Asp
```

```
                    405                 410                 415
Glu Leu Met His Gln Lys Arg Thr Ala Met Phe Gln Asp Pro Gln Glu
                420                 425                 430

Arg Pro Arg Lys Leu Pro His Leu Cys Thr Glu Leu Gln Thr Thr Ile
            435                 440                 445

His Asp Ile Ile Leu Glu Cys Val Tyr Cys Lys Gln Gln Leu Leu Arg
        450                 455                 460

Arg Glu Val Tyr Asp Phe Ala Phe Arg Asp Leu Cys Ile Val Tyr Arg
465                 470                 475                 480

Asp Gly Asn Pro Tyr Ala Val Cys Asp Lys Cys Leu Lys Phe Tyr Ser
                485                 490                 495

Lys Ile Ser Glu Tyr Arg Tyr Tyr Cys Tyr Ser Val Tyr Gly Thr Thr
            500                 505                 510

Leu Glu Gln Gln Tyr Asn Lys Pro Leu Cys Asp Leu Leu Ile Arg Cys
        515                 520                 525

Ile Asn Cys Gln Lys Pro Leu Cys Pro Glu Glu Lys Gln Arg His Leu
        530                 535                 540

Asp Lys Lys Gln Arg Phe His Asn Ile Arg Gly Arg Trp Thr Gly Arg
545                 550                 555                 560

Cys Met Ser Cys Cys Arg Ser Ser Arg Thr Arg Glu Thr Gln Leu
                565                 570                 575

<210> SEQ ID NO 13
<211> LENGTH: 1731
<212> TYPE: DNA
<213> ORGANISM: artificial
<220> FEATURE:
<223> OTHER INFORMATION: CRT-E6

<400> SEQUENCE: 13
atgctgctcc ctgtgccgct gctgctcggc ctgctcggcc tggccgccgc cgagcccgtc      60
gtctacttca aggagcagtt tctggacgga gatgggtgga ccgagcgctg gatcgaatcc     120
aaacacaagt ccgatttggg caaattcgtc ctcagttcgg gcaagttcta cggcgatcag     180
gagaaagata aagggctgca gaccagccag gacgcccgct tctacgccct gtcggcccga     240
ttcgagccgt tcagcaacaa gggccagcca ctggtggtgc agttcaccgt gaaacacgag     300
cagaacattg actgcggggg cggctacgtg aagctgtttc cggccggcct ggaccagaag     360
gacatgcacg gggactctga gtacaacatc atgtttggtc ctgacatctg tggccccggc     420
accaagaagg ttcacgtcat cttcaactac aagggcaaga acgtgctgat caacaaggac     480
atccgttgca aggacgacga gttcacacac ctgtacacgc tgatcgtgcg gccggacaac     540
acgtatgagg tgaagattga acagccag gtggagtcgg ctccctgga ggatgactgg     600
gacttcctac cccccaagaa gataaaggac ccagatgcct cgaagcctga agactgggac     660
gagcgggcca agatcgacga ccccacggac tccaagcccg aggactggga caagcccgag     720
cacatccccg acccggacgc gaagaagccc aagactgggg acgaagaaat ggacggagag     780
tgggagccgc cggtgattca gaaccccgag tacaagggtg agtggaagcc gcggcagatc     840
gacaaccccg attacaaagg cacctggatc caccccgaaa tcgacaaccc cgagtactcg     900
cccgacgcta acatctatgc ctacgacagc tttgccgtgc tgggcttgga cctctggcag     960
gtcaagtcgg gcaccatctt cgacaacttc ctcatcacca cgatgaggc gtacgcagag    1020
gagtttggca acgagacgtg gggcgtcacc aagacggccg agaagcagat gaagacaag    1080
caggacgagg agcagcggct gaaggaggag gaggaggaga agaagcggaa ggaggaggag    1140
```

```
gaggccgagg aggacgagga ggacaaggac gacaaggagg acgaggatga ggacgaggag    1200
gacaaggacg aggaggagga ggaggcggcc gccggccagg ccaaggacga gctgatgcac    1260
caaaagagaa ctgcaatgtt tcaggaccca caggagcgac ccagaaagtt accacagtta    1320
tgcacagagc tgcaaacaac tatacatgat ataatattag aatgtgtgta ctgcaagcaa    1380
cagttactgc gacgtgaggt atatgacttt gcttttcggg atttatgcat agtatataga    1440
gatgggaatc catatgctgt atgtgataaa tgtttaaagt tttattctaa aattagtgag    1500
tatagacatt attgttatag tttgtatgga acaacattag aacagcaata caacaaaccg    1560
ttgtgtgatt tgttaattag gtgtattaac tgtcaaaagc cactgtgtcc tgaagaaaag    1620
caaagacatc tggacaaaaa gcaaagattc cataatataa ggggtcggtg gaccggtcga    1680
tgtatgtctt gttgcagatc atcaagaaca cgtagagaaa cccagctgta a             1731
```

What is claimed:

1. A method of inducing an immune response against a pathogen comprising:
first administering to a patient an effective amount of a virus-like particle ("VLP") comprising a papillomavirus L1 protein or polypeptide and a chimeric protein or polypeptide, the chimeric protein or polypeptide comprising a papillomavirus L2 polypeptide and a protein or polypeptide fragment comprising a first pathogen-specific epitope, which VLP is devoid of DNA; and
second administering to the patient a DNA molecule encoding a protein or polypeptide comprising the pathogen-specific epitope, wherein delivery of the DNA molecule is not dependent on VLP-mediated uptake;
wherein said first and second administering are carried out at about the same time and are effective to induce a synergistic immune response against the pathogen, as compared to the first and second administering alone.

2. The method according to claim 1 wherein the L2 polypeptide is a full-length L2 protein.

3. The method according to claim 1 wherein the L2 polypeptide is an N-terminal fragment of L2 protein.

4. The method according to claim 1 wherein the pathogen is a bacterium, a virus, a fungus, or a protozoan.

5. The method according to claim 1 wherein the DNA molecule is present in a plasmid or expression vector.

6. The method according to claim 1 wherein the VLP is a chimeric HPV-16 L1/L2-Nef fusion VLP and the DNA molecule encodes a polypeptide comprising an HIV Nef epitope.

7. The method according to claim 1 wherein the VLP is a chimeric HPV-16 L1/L2-HPV-E6 fusion VLP and the DNA molecule encodes a polypeptide comprising an HPV16 E6 epitope.

8. The method according to claim 1 wherein said first and second administering are carried out at anatomically distinct sites.

9. The method according to claim 1 further comprising repeating either said first administering or said second administering or both.

10. A method of inducing an immune response against a pathogen comprising:
administering to a patient an effective amount of a papillomavirus virus-like particle ("VLP") comprising an L1 protein or polypeptide and a chimeric protein or polypeptide, the chimeric protein or polypeptide comprising an L2 polypeptide and a protein or polypeptide fragment comprising a pathogen-specific epitope; and
separately administering to the patient a DNA molecule encoding the protein or polypeptide comprising the pathogen-specific epitope;
wherein said administering the VLP and said separately administering the DNA molecule are carried out at about the same time and are effective to induce a synergistic immune response against the pathogen as compared to the additive effects of said administering the VLP and said separately administering the DNA molecule alone.

11. The method according to claim 10 wherein the L2 polypeptide is a full-length L2 protein.

12. The method according to claim 10 wherein the L2 polypeptide is a truncated L2 protein.

13. The method according to claim 10 wherein the L2 polypeptide is an N-terminal fragment of L2 protein.

14. The method according to claim 10 wherein the pathogen is a bacterium, a virus, a fungus, or a protozoan.

15. The method according to claim 10 wherein the VLP is a chimeric HPV-16 L1/L2-Nef fusion VLP and the pathogen-specific epitope is an HIV Nef epitope.

16. The method according to claim 10 wherein the VLP is a chimeric HPV-16 L1/L2-HPV-E6 fusion VLP and the pathogen-specific epitope is an HPV E6 epitope.

17. The method according to claim 10 further comprising repeating one or both of said administering the VLP or said separately administering the DNA molecule.

18. The method according to claim 10 wherein the DNA molecule is present in a plasmid or expression vector.

19. The method according to claim 10 wherein said administering the VLP and said separately administering the DNA molecule are carried out at anatomically distinct sites.

* * * * *

UNITED STATES PATENT AND TRADEMARK OFFICE
CERTIFICATE OF CORRECTION

| | |
|---|---|
| PATENT NO. | : 8,778,351 B2 |
| APPLICATION NO. | : 12/439338 |
| DATED | : July 15, 2014 |
| INVENTOR(S) | : Rose et al. |

It is certified that error appears in the above-identified patent and that said Letters Patent is hereby corrected as shown below:

In the Claims

In claim 1, at col. 79, line 30, delete "first".

Signed and Sealed this
Eleventh Day of November, 2014

Michelle K. Lee
*Deputy Director of the United States Patent and Trademark Office*